US012590074B2

(12) United States Patent
Helal

(10) Patent No.: US 12,590,074 B2
(45) Date of Patent: Mar. 31, 2026

(54) METHOD OF FIXATING CARBON DIOXIDE TO SUBSTITUTED OXAZOLIDINONES

(71) Applicant: KING FAHD UNIVERSITY OF PETROLEUM AND MINERALS, Dhahran (SA)

(72) Inventor: Aasif Helal, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 519 days.

(21) Appl. No.: 18/329,092

(22) Filed: Jun. 5, 2023

(65) Prior Publication Data

US 2024/0400524 A1 Dec. 5, 2024

(51) Int. Cl.

*C07D 263/04* (2006.01)
*C07D 239/00* (2006.01)
*C07D 263/06* (2006.01)
*C07D 263/58* (2006.01)

(52) U.S. Cl.

CPC ......... *C07D 263/04* (2013.01); *C07D 239/00* (2013.01); *C07D 263/06* (2013.01); *C07D 263/58* (2013.01)

(58) Field of Classification Search

CPC .. C07D 263/04; C07D 239/00; C07D 263/06; C07D 263/58

See application file for complete search history.

(56) References Cited

U.S. PATENT DOCUMENTS

| | | | | |
|---|---|---|---|---|
| 6,239,152 B1 | 5/2001 | Gordeev et al. | | |
| 8,940,905 B2 * | 1/2015 | Savonnet | ................ | C07F 5/003 548/104 |
| 9,200,010 B2 * | 12/2015 | Savonnet | ................ | C07F 5/003 |
| 11,498,906 B1 | 11/2022 | Helal et al. | | |
| 11,529,621 B1 | 12/2022 | Helal et al. | | |
| 2025/0250248 A1 * | 8/2025 | Helal | ................... | B01J 31/1691 |

FOREIGN PATENT DOCUMENTS

KR 10-1638049 B1 7/2016

OTHER PUBLICATIONS

Chong; Langmuir 2019, 35, 2, 495-503. https://doi.org/10.1021/acs.langmuir.8b03153 (Year: 2019).*

Helal; Journal of CO2 Utilization 2021, 50, 101603. https://doi.org/10.1016/j.jcou.2021.101603 (Year: 2021).*

Helal; Catal Lett 2023, 153, 2883-2891. Published Nov. 7, 2022. https://doi.org/10.1007/s10562-022-04213-x (Year: 2022).*

Li; Chem. Commun., 2021, 57, 10803. https://doi.org/10.1039/D1CC04371D (Year: 2021).*

Liu; Nano Res. 2023, 16, 181-188. Published Jul. 23, 2022. https://doi.org/10.1007/s 12274-022-4664-0 (Year: 2022).*

Tian; Inorg. Chem. 2021, 60, 20, 15383-15389. https://doi.org/10.1021/acs.inorgchem.1c02034 (Year: 2021).*

Volkringer; Inorg. Chem. 2008, 47, 11892-11901. https://doi.org/10.1021/ic801624v (Year: 2008).*

Xue-Rui Tian, et al., "Efficient Cycloaddition of $CO_2$ and Aziridines Activated by a Quadruple-Interpenetrated Indium-Organic Framework as a Recyclable Catalyst", Inorganic Chemistry, vol. 60, Issue 20, Sep. 30, 2021, pp. 15383-15389 (Abstract only).

Yang Li, et al., "Amino and triazole-containing metal-organic frameworks for highly efficient $CO_2$ fixation", Chemical Communications, vol. 57, Issue 82, Sep. 20, 2021, pp. 10803-10806 (Abstract only).

* cited by examiner

*Primary Examiner* — Daniel R Carcanague

(74) *Attorney, Agent, or Firm* — Oblon, McClelland, Maier & Neustadt, L.L.P.

(57) ABSTRACT

A method of fixating carbon dioxide ($CO_2$) to form a substituted oxazolidinone is described. The method includes mixing a metal-organic framework (MOF), at least one epoxide, and at least one aromatic amine to form a mixture. The method further includes contacting the mixture with a gas stream containing $CO_2$ to react the $CO_2$ in the gas stream with the epoxide and the aromatic amine to form a substituted oxazolidinone. The MOF is a MIL-68(In)—X MOF. X is of formula (I):

(I)

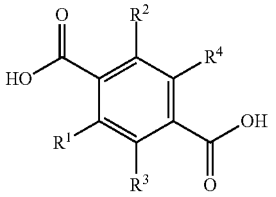

where at least one of $R^1$ to $R^4$ is an amine-containing group, and $R^1$ to $R^4$ are independently an amine-containing group or a hydrogen.

20 Claims, 16 Drawing Sheets

METHOD OF FIXATING CARBON DIOXIDE TO SUBSTITUTED OXAZOLIDINONES

STATEMENT OF ACKNOWLEDGEMENT

The inventors acknowledge the support provided by the Saudi Aramco-sponsored Chair Program on Carbon Capture and Utilization through Grant ORCP2390. The inventors acknowledge the support provided by the Interdisciplinary Research Center for Hydrogen and Energy Storage, King Fahd University of Petroleum and Minerals, Saudi Arabia, through Project INHE2205.

BACKGROUND

Technical Field

The present disclosure is directed to a metal-organic framework (MOF), and particularly to a triazole-functionalized indium-based MOF as a catalyst for chemical fixation of carbon dioxide ($CO_2$) to a substituted oxazolidinone and a method of preparing the same.

Description of Related Art

The 'background' description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

A breakneck increase in the anthropogenic carbon dioxide ($CO_2$) in the atmosphere has lead to various environmental and societal concerns such as global warming, glacier retreat, ocean acidification, thawing of frozen soil, and unpredictable weather patterns. In addition, the dependence on fossil fuels to meet the world's burgeoning energy demands in industries and transportation has resulted in sufficient accretion of $CO_2$ in the atmosphere. Thus, to diminish the level of $CO_2$ in the atmosphere, focus on the sustainable carbon capture and storage (CCS), in the form of $CO_2$, and the consecutive utilization of $CO_2$ as a C1 source for manufacturing fine chemicals has become popular. All the chemical combustion reactions result in the generation of $CO_2$, an inexpensive, abundant, and thermodynamically stable gas (bond energy of +805 kilojoules per mole (kJ/mol)), as a final product. The inherent inertness of $CO_2$, however, is a significant synthetic challenge. To overcome the inherent inertness of $CO_2$, several suitable catalysts have been designed for the functionalization of the $CO_2$ into value-added energy-related products such as N,N'-disubstituted urea, dimethyl carbonates, cyclic carbonates, formic acid, methane, methanol, olefin, oxazolidinones, and other carbon-containing products under environmental-friendly conditions.

Oxazolidinones are essential five-membered heterocyclic compounds containing nitrogen and oxygen. They are extensively used as an intermediate in different organic syntheses, and as antibacterial and antimicrobial agents such as tedizolid, linezolid, and radezolid. They are also a key structural unit in pharmaceutical and agrochemical industries. Thus, many methods have been developed for the synthesis of oxazolidinones. The conventional synthetic method for synthesizing oxazolidinones uses phosgene or isocyanates as the source for the carbonyl carbon. These materials are highly toxic and in order to avoid the toxicity of phosgene and isocyanates as starting materials, $CO_2$ or cyclic carbonates are used as the source of the carbonyl carbon in a variety of reactions. These reactions include dehydration of vicinal amino alcohols with $CO_2$, the cycloaddition of aziridines to $CO_2$, aminolysis of cyclic carbonates, and cyclization of unsaturated amines with $CO_2$. Most of these methods use carbon dioxide under high pressure, expensive metal catalysts, and are non-recyclable. Therefore, there exists a need for efficient methods to be developed to reduce or eliminate the above limitations substantially.

Accordingly, it is one object of the present disclosure to provide a method for fixating carbon dioxide in the form of an oxazolidone.

SUMMARY

In an exemplary embodiment, a method of fixating carbon dioxide ($CO_2$) to form a substituted oxazolidinone is described. The method includes mixing a metal-organic framework (MOF), at least one epoxide, and at least one aromatic amine to form a mixture. The method further includes contacting the mixture with a gas stream containing $CO_2$ to react the $CO_2$ in the gas stream with the epoxide and the aromatic amine to form a substituted oxazolidinone. The MOF is a MIL-68(In)—X MOF. X is of formula (I):

(I)

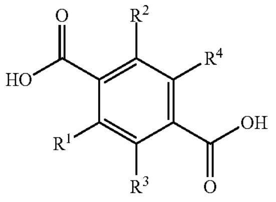

Where at least one of $R^1$ to $R^4$ is an amine-containing group, and $R^1$ to $R^4$ is independently an amine-containing group or a hydrogen.

In some embodiments, X is:

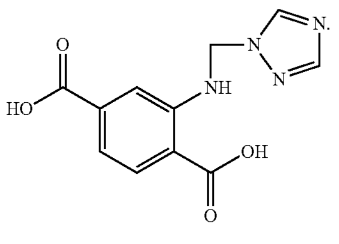 [SMILES: O=C(O)c1ccc(C(=O)O)c(NCn2cncn2)c1]

In some embodiments, the MIL-68(In)—X MOF includes a terephthalate linker with a triazole-based moiety.

In some embodiments, the method includes forming the MIL-68(In)—X MOF by functionalizing the terephthalate linker with the triazole-based moiety. Functionalizing the terephthalate linker includes reacting a terephthalic acid, a 1,2,4-triazole moiety, and formaldehyde to form a first compound; and further hydrolyzing the first compound under alkaline conditions to form the terephthalate linker with the triazole-based moiety.

In some embodiments, the method includes contacting the mixture in the presence of the MIL-68(In)—X MOF, repeatedly, at least 5 times and up to 7 times. The yield of the product after final contact is at least 95 percent of the yield of a first contact based on an oxazolidinone product yield based on a mol percent.

In some embodiments, the MIL-68(In)—X MOF is in the form of particles having a surface area of 350-450 square meters per gram ($m^2/g$).

In some embodiments, the MIL-68(In)—X MOF has an average carbon dioxide uptake of 40 to 90 grams per cubic centimeter (cc $g^{-1}$) at 1 bar at 273 kelvin (K).

In some embodiments, the MIL-68(In)—X MOF has an average isosteric heat of adsorption of 20 to 40 kilojoules per mole (kJ mol-1).

In some embodiments, the epoxide is at least one selected from a group consisting of 1,2-epoxyhexane, 1,2-epoxypropane, 1,2-epoxybutane, allyl glycidyl ether, styrene oxide, phenyl glycidyl ether, and epoxycyclohexane.

In some embodiments, the aromatic amine is at least one selected from a group consisting of aniline, 4-nitroaniline, toluidine, para-anisidine, 4-chloroaniline, 4-aminothiophenol, adenine, and benzylamine.

In some embodiments, the mixture has a 1:1 to 1:5 molar ratio of the MIL-68(In)—X MOF to the aromatic amine.

In some embodiments, the mixture has a 1:1 to 1:10 molar ratio of the aromatic amine to the epoxide.

In some embodiments, the method includes contacting the mixture at a temperature of 40 to 150° C.

In some embodiments, the method includes contacting the mixture at a pressure of 0.5 to 10 bar of carbon dioxide.

In some embodiments, the method includes contacting the mixture for 8 to 20 hours.

In some embodiments, 65 to 95 percent of the aromatic amine is converted into the substituted oxazolidinone based on a mol percent.

In some embodiments, the MIL-68(In)—X MOF is microporous.

In some embodiments, the percent yield is calculated by proton nuclear magnetic resonance spectroscopy.

In some embodiments, the substituted oxazolidinone is of formula (II), (II)

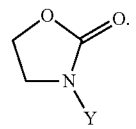

X is selected from a group consisting of an alkyl chain, an alkoxy group, an aromatic group, a methoxybenzene, and a cyclohexane. Y is selected from a group consisting of benzene, para-substituted benzene, and adenine.

In some embodiments, a cocatalyst is not present.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
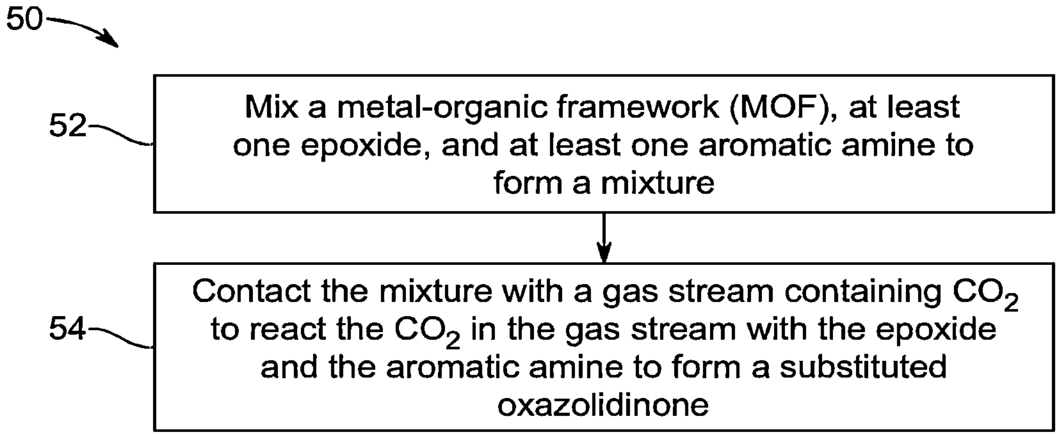
FIG. 1A is a flow chart of a method of fixating $CO_2$ to form a substituted oxazolidinone, according to embodiments of the present disclosure.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the word "include," and its variants, is intended to be non-limiting, such that recitation of items in a list is not to the exclusion of other like items that may also be useful in the materials, compositions, devices, and methods of this technology.

The description and specific examples, while indicating embodiments of the technology, are intended for purposes of illustration only and are not intended to limit the scope of the technology. Moreover, the recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

The term "epoxide", as used herein, unless otherwise specified, refers to a cyclic ether with a three-atom ring. Exemplary epoxides that may be used include epoxy cyclohexane, 1,2-epoxypropane, 1,2-epoxybutane, 1,2-epoxyhexane, styrene oxide, allyl glycidyl ether, and phenyl glycidyl ether.

The term "oxazolidinone", as used herein, unless otherwise specified, is a heterocyclic organic compound containing both nitrogen and oxygen in a 5-membered ring.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino ($-NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkyl sulfonyl, aryl sulfonyl, arylalkylsulfonyl, sulfonamide (e.g., $-SO_2NH_2$), substituted sulfonamide (e.g., $-SO_2$NHalkyl, $-SO_2$NHaryl, $-SO_2$NHarylalkyl, or cases where there are two substituents on one nitrogen selected from alkyl, aryl, or alkylalkyl), nitro, cyano, carboxy, unsubstituted amide (i.e., $-CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted and may be either unprotected, or protected as necessary, as known to those skilled in the art.

Throughout the specification and the appended claims, a given chemical formula or name shall encompass all isomers (stereo and optical isomers and racemates) thereof where such isomers exist. Unless otherwise indicated, all chiral (enantiomeric and diastereomeric) and racemic forms are within the scope of the disclosure. Many geometric isomers of C═C double bonds, C═N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions, the end products of the present disclosure are obtained either in free (neutral) or salt form. Both the free form and salts of products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein "metal-organic frameworks" or MOFs are compounds having a lattice structure made from (i) a cluster of metal ions as vertices ("cornerstones") ("secondary building units" or SBUs) which are metal-based inorganic groups, for example metal oxides and/or hydroxides, linked together by (ii) organic linkers. The linkers are usually at least bidentate ligands which coordinate to the metal-based inorganic groups via functional groups such as carboxylates and/or amines. MOFs are considered coordination polymers made up of (i) the metal ion clusters and (ii) linker building blocks.

As used herein, the term "amines", unless otherwise specified, refers to the compounds and functional groups that contain a basic nitrogen atom with a lone pair. Amines are formally derivatives of ammonia ($NH_3$), where one or more hydrogen atoms have been replaced by a substituent such as an alkyl or aryl group (these may respectively be called alkylamines and arylamines; amines in which both types of substituent are attached to one nitrogen atom may be called alkylarylamines). Amines may include amino acids, biogenic amines, trimethylamine, and aniline. Inorganic derivatives of ammonia are also called amines, such as monochloramine ($NClH_2$).

The term "aromatic compounds" or "aromatic rings", as used herein, unless otherwise specified, refers to hydrocarbon rings that, by the theory of Hickel, have a cyclic, delocalized (4n+2) pi-electron system. Non-limiting examples of aromatic compounds include benzene, benzene derivatives, compounds having at least one benzene ring in their chemical structure, toluene, ethylbenzene, p-xylene, m-xylene, mesitylene, durene, 2-phenylhexane, biphenyl, phenol, aniline, nitrobenzene, and the like As used herein, the term "aromatic amine" refers to the organic compound consisting of an aromatic ring attached to an amine. It is a broad class of compounds that encompasses anilines, but also many more complex aromatic rings and many amine substituents beyond $NH_2$.

The term "alkyl", as used herein, unless otherwise specified, refers to a straight, branched, or cyclic, saturated aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-propylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as cyclic alkyl groups (cycloalkyls) such as cyclopropyl, cyclobutyl, cyclopentyl, cyclohexyl, norbornyl, and adamantyl.

As used herein, the term 'alkoxy' refers to an alkyl group which is singularly bonded to oxygen; thus R—O, where R has $C_1$-$C_{10}$ carbon atoms.

The term "aryl", as used herein, unless otherwise specified, refers to a carbocyclic aromatic monocyclic group containing 6 carbon atoms which may be further fused to a second 5- or 6-membered carbocyclic group which may be aromatic, saturated, or unsaturated. Aryl includes, but is not limited to, phenyl, anthracenyl, indanyl, 1-napthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above), that is substituted with an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

Aspects of the present invention are directed towards the synthesis and characterization of a triazole-functionalized indium-based metal-organic framework (MOF) or herein referred to as the "MOF", and its application of fixating carbon dioxide ($CO_2$) to form a substituted oxazolidinone. The MOF was characterized by powder X-ray diffraction (PXRD), Fourier transform infrared (FTIR) spectroscopy, scanning electron microscopy (SEM), thermogravimetric analysis (TGA), X-ray photoelectric emission spectroscopy (XPS), $N_2$ adsorption isotherm, $CO_2$ adsorption isotherm, and $CO_2$ temperature programmed desorption (TPD). In the present disclosure, an efficient approach to achieve net-zero greenhouse gas emissions by 100% atom-economical conversion of the greenhouse gas carbon dioxide ($CO_2$) to cost-effective, less toxic cyclic carbonates that can act as green solvents and abundant $C_1$ synthons in organic synthesis is described. Particularly, an indium metal-organic framework (MOF), functionalized with a triazole, MIL-68 (In)—NHTr, is used as a heterogeneous catalyst in the fixation of $CO_2$ with epoxides and aromatic amines for the synthesis of oxazolidinones, more particularly in 87% yield. The catalyst is preferably used at ambient pressure without the presence of solvents and without the presence of any cocatalysts. The present heterogeneous catalyst is applied for a wide range of epoxides and aromatic amines to give oxazolidinones in an efficient yields. Results indicate that the MOF provides efficient separation, better sample handling, and better reusability (more particularly, the catalyst is recyclable and can be reused for seven consecutive cycles). Furthermore, the synergistic acid-base effect of indium SBU and the triazole of MIL-68(In)—NHTr make this a better catalyst in comparison to the conventionally used catalysts.

FIG. 1A illustrates a flow chart of a method 50 of fixating $CO_2$ to a substituted oxazolidinone. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes mixing a metal-organic framework (MOF), at least one epoxide, and at least one aromatic amine to form a mixture. A cocatalyst is not present. In some embodiments, the MOF may be any indium-based MOF. The MOF of the present disclosure is preferably based on indium ions (made from indium ion clusters), referred to herein as a indium-based metal-organic framework (In-MOF). The In-MOF herein is intended to cover any MOF which contains predominantly indium ions with respect to the total metal ion content. The In-MOFs of the disclosure include indium ion clusters (cornerstones) which are indium inorganic groups, typically indium ions connected by bridging oxygen groups, bridging hydroxide groups, or both. These indium ion clusters are further coordinated to at least one linker. In some cases, the indium ion clusters may be further connected to non-bridging modulator species, complexing reagents or ligands (e.g., sulfates or carboxylates such as formate, benzoate, acetate, etc.) and/or solvent molecules (e.g., $H_2O$). In an embodiment, the indium ion cluster is considered to have an octahedron shape. In addition to the indium ion clusters (cornerstones), the In-MOFs of the present disclosure are formed from at least one linker, which may be bidentate, tridentate, or tetradentate, and which links together adjacent indium ion clusters to form a coordinated network. In a preferred embodiment, the linker is of formula (I). In some embodiments, the In-MOF is a MIL-68(In)—X MOF. The MIL-68 (In)—X MOF is microporous. The MIL-68(In)—X MOF includes a terephthalate linker with a triazole-based moiety. X is of formula (I):

(I)

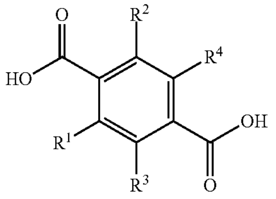

Where at least one of $R^1$ to $R^4$ is an amine-containing group, and $R^1$ to $R^4$ are independently an amine-containing group or a hydrogen. In some embodiments, two of $R^1$ to $R^4$ are amine-containing groups and two are hydrogens. In some embodiments, three of $R^1$ to $R^4$ are amine-containing groups and one is a hydrogen. In some embodiments, three of $R^1$ to $R^4$ are hydrogens and one is an amine-containing group (depicted below). In some embodiments, X is:

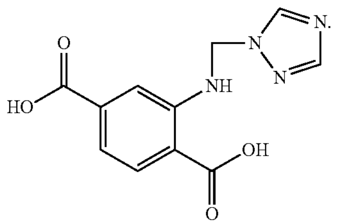 [SMILES: O=C(O)c1ccc(C(=O)O)c(NCn2cncn2)c1]

In some embodiments, the epoxide is any epoxide known in the art substituted at one carbon of the three membered ring. In an embodiment, the epoxide is at least one selected from a group consisting of 1,2-epoxyhexane, 1,2-epoxypropane, 1,2-epoxybutane, allyl glycidyl ether, styrene oxide, phenyl glycidyl ether, and epoxycyclohexane. In some embodiments, the aromatic amine is any aromatic amine known in the art. In an embodiment, the aromatic amine is at least one selected from a group consisting of aniline, 4-nitroaniline, toluidine, para-anisidine, 4-chloroaniline, 4-aminothiophenol, adenine, and benzylamine. In an embodiment, the mixture has a 1:1 to 1:5 molar ratio of the MIL-68(In)—X MOF to the aromatic amine, preferably 1 to 4, 1 to 3, 1 to 2, or 1 to 1. In some embodiments, the mixture has a 1:1 to 1:10 molar ratio of the aromatic amine to the epoxide. The MIL-68(In)—X MOF has a Brunauer-Emmett-Teller (BET) surface area of 350-450 square meters per gram ($m^2/g$), more preferably 380 to 410 $m^2/g$, and yet more preferably about 405 $m^2/g$. In some embodiment, the MIL-68(In)—X MOF may have a pore size of 0.5 to 2.0 nm, preferably 1.0 to 1.7 nm, preferably 1.2 to 1.5 nm. Both the BET surface area and pore size of the MOF of the present disclosure are smaller than those reported due to the presence of the amine group(s) in the pores.

The MOF of the present disclosure has an effective adsorption capacity for $CO_2$. In some embodiments, the MOF may have an average carbon dioxide uptake of 60 to 90 gram per cubic centimeter ($cm^3\ g^{-1}$), more preferably 75 to 85 $cm^3\ g^{-1}$, and yet more preferably about 83.5 $cm^3\ g^{-1}$ at 1 bar at 273 kelvin (K). In some embodiments, the MOF may have a $CO_2$ uptake capacity of 35 to 55 $cm^3\ g^{-1}$, preferably 42 to 48 $cm^3\ g^{-1}$, and more preferably about 46 $cm^3\ g^{-1}$ at 1 bar at 298 K. In some embodiments, the MOF may have an average isosteric heat of adsorption of 20 to 40 kilojoules per mole ($kJ\ mol^{-1}$), more preferably 30 to 35 $kJ\ mol^{-1}$, and yet more preferably about 32.5 $kJ\ mol^{-1}$. In some embodiments, the MOF is stable up to about 425° C., preferably 100 to 425° C., preferably 200 to 400° C., or 250 to 350° C.

At step 52, the method 50 includes contacting the mixture with a gas stream containing $CO_2$ to react the $CO_2$ in the gas stream with the epoxide and the aromatic amine to form a substituted oxazolidinone. The substituted oxazolidinone is of formula (II), (II)

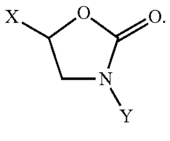

X is selected from a group consisting of an alkyl chain, an alkoxy group, an aromatic group, a methoxybenzene, and a cyclohexane. Y is selected from a group consisting of a benzene, a para-substituted benzene, and an adenine. 65 to 95% of the aromatic amine is converted into the substituted oxazolidinone. In some embodiments, $CO_2$ may be sourced from large fossil fuel or biomass electricity power plants, industries with major $CO_2$ emissions, natural gas processing, synthetic fuel plants, and fossil fuel-based hydrogen production plants. In some embodiments, the gas stream is at least 20 percent by volume (v. %) $CO_2$, preferably at least 30 v. %, 40 v. %, 50 v. %, 60 v. %, 70 v. %, 80 v. %, 90 v. %, or 100 v. % $CO_2$ based on a total volume of the gas stream. In some embodiments, other possible gasses in the gas stream may include but is not limited to, nitrogen, hydrogen, oxygen, water (vapor), carbon monoxide, hydrocarbons having 1-4 carbon atoms (e.g., methane, ethane, ethylene, acetylene, propane, propylene, butane, iso-butane), nitrogen oxides (i.e., nitric oxide, nitrous oxide, nitrogen dioxide), and noble gases (e.g., helium, neon, argon, krypton, xenon), including mixtures thereof.

In some embodiments, the method 50 includes contacting the mixture with the gas stream containing $CO_2$ at a temperature of 40 to 150° C., more preferably 75 to 90° C., and yet more preferably about 85° C. In some embodiments, the method 50 includes contacting the mixture with the gas stream containing $CO_2$ at a pressure of 0.5 to 10 bar, more preferably 0.2 to 1.2 bar, and yet more preferably about 1 bar of carbon dioxide. In some embodiments, the method 50 includes contacting the mixture with the gas stream containing $CO_2$ for 8 to 20 hours, more preferably 10 to 14 hours, and yet more preferably 12 hours to form the substituted oxazolidinone. In an embodiment, 65 to 99%, preferably 80 to 95%, or 85 to 90% of the aromatic amine is converted in the substituted oxazolidinone. In some embodiments, the method 50 includes contacting the mixture repeatedly in the presence of the MIL-68(In)—X MOF at least 5 consecutive times and up to 7 consecutive times. The yield of a final product, after the last consecutive contact, is at least 95 percent of the yield of a first contact based on an oxazolidinone product yield. The percent yield is calculated by proton nuclear magnetic resonance spectroscopy.

Figure 1B:
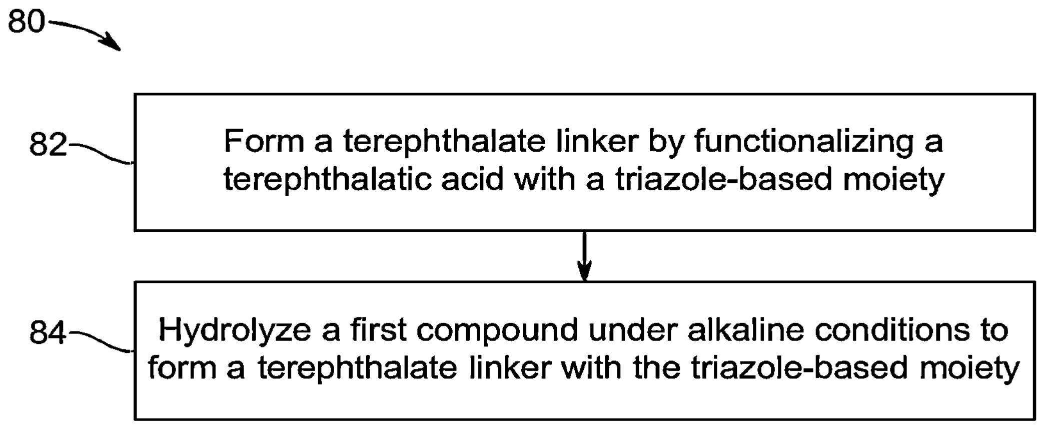
FIG. 1B is a flow chart of a method of forming MIL-68 (In)—X MOF, according to embodiments of the present disclosure.

FIG. 1B illustrates a flow chart of a method 80 of forming a terephthalate linker. The order in which the method 80 is described is not intended to be construed as a limitation, and any number of the described method steps can be combined in any order to implement the method 80. Additionally, individual steps may be removed or skipped from the method 80 without departing from the spirit and scope of the present disclosure.

At step 82, the method 80 includes functionalizing a terephthalate acid with a triazole-based moiety. As used herein, the term "functionalization" refers to the addition of functional groups to a compound by chemical synthesis. The functionalizing includes reacting a terephthalic acid, a 1,2,4-triazole moiety, and formaldehyde to form a first compound. In a preferred embodiment, the terephthalic acid may be 2-aminoterephthalic acid. In some embodiments, the terephthalic acid may be any terephthalic acid known in the art including, but not limited to, terephthalic acid, 2-fluoroterephthalic acid, 2-chloroterephthalic acid, 2-bromoterephthalic acid, 2-iodoterephthalic acid, 2-hydroxyterephthalic acid, 2,5-aminoterephthalic acid, 2,5-fluoroterephthalic acid, 2,5-chloroterephthalic acid, 2,5-bromoterephthalic acid, 2,5-iodoterephthalic acid, 2,5-hydroxyterephthalic acid, and the like. The terephthalic acid may be monosubstituted, disubstituted, trisubstituted, and 4-substituted. In some embodiments, one or more carboxylic acids of the terephthalic acid may be protected via an esterification process with, for example, methanol. In an embodiment, the esterification process may produce, for example, dimethyl terephthalate, dimethyl 2-aminoterephthalate, and the like. In some embodiments, the 1,2,4-triazole moiety may be a 1,2,3-triazole moiety and the like. In some embodiments, the 1,2,4-triazole moiety may be subtituted with one or more amines, one or more amides, one or more hydroxyls, one or more halos (e.g., —F, —Cl, —Br, —I), one or more thiols, one or more alkyls, one or more aryls, a combination thereof, and anything known in the art. The first compound, produced from the terephthalic acid, the 1,2,4-triazole moiety, and formaldehyde, may be likewise substituted. In an embodiment, the first compound is a dimethyl terephthalate functionalized with the 1,2,4-triazole moiety.

At step 84, the method 80 includes hydrolyzing the first compound under alkaline conditions to form the terephthalate linker with the triazole-based moiety. As used herein, the term "hydrolyzing" refers to the chemical reaction that uses water to break down a compound. In an embodiment, the first compound consists of one or more methyl ethers which are hydrolyzed to produce one or more carboxylic acids. In an embodiment, the terephthalate linker with the triazole-based moiety is terephthalic acid with the triazole based moiety.

EXAMPLES

The following examples describe and demonstrate exemplary embodiments of the method 50 of fixating $CO_2$ to the substituted oxazolidinone described herein. The examples are provided solely for the purpose of illustration and are not to be construed as limitations of the present disclosure, as many variations thereof are possible without departing from the spirit and scope of the present disclosure.

Materials and Methods

Indium nitrate hydrate (99.9% purity), 2-aminoterephthalic acid (98% purity), 1,2,4-triazole (98% purity), formaldehyde (99% purity), methanol (99.9% purity), ethanol (97.2% purity), N,N-dimethylformamide (DMF; 99.8% purity), dichloromethane (99.8% extra dry grade), potassium hydroxide (98% purity), 1,2-epoxypropane (99.5% purity), 1,2-epoxybutane (99.0% purity), 1,2-epoxyhexane (97.0% purity), epichlorohydrin (99.0% purity), styrene oxide (97.0% purity), allyl glycidyl ether (99.0% purity), phenyl glycidyl ether (99.0% purity), tetrabutylammonium bromide (99.0% purity), tetrabutylammonium iodide (99.0% purity), tetrabutylammonium chloride (99.0% purity), hexane (95.0% purity), and ethyl acetate (99.0% purity) were purchased from Sigma Aldrich Corporation. Nuclear magnetic resonance (NMR) solvents: dimethyl sulfoxide-$d_6$ (DMSO-$d_6$; 99.9% purity) were purchased from Cambridge Isotope. All chemicals were used without further purification. Water was double distilled and filtered through a Millipore membrane. Analytical thin-layer chromatography (TLC) was performed on pre-coated silica gel 60 $F_{254}$ plates. Visualization on TLC was achieved by the use of UV light (254 nanometers (nm)). Flash column chromatography was undertaken on silica gel (400-630 mesh).

MOFs are structurally tunable extended crystalline porous materials prudently designed by the coordination-driven integration between different types of functionalized linkers and metal ions or clusters. Diversifying these two structural components bestows MOFs with resilience in the design of channel type and sizes, as well as functionalization of the surface, pores, and open metal sites. These render MOFs as excellent porous functional materials for application in catalysis, sensors, $CO_2$ capture and utilization, and biological applications. Indium-based MOFs, due to electronic configuration, form different secondary building units (SBU), such as $[In(O_2)_4]$, $[In(OH)]$, and $[In_3O_4(O_2)_6]$. The strong affinity of dicarboxylate linkers towards $In^{3+}$ makes In-based MOFs (In-MOFs) stable towards the air, water, temperature, and common organic solvents.

Figure 2:
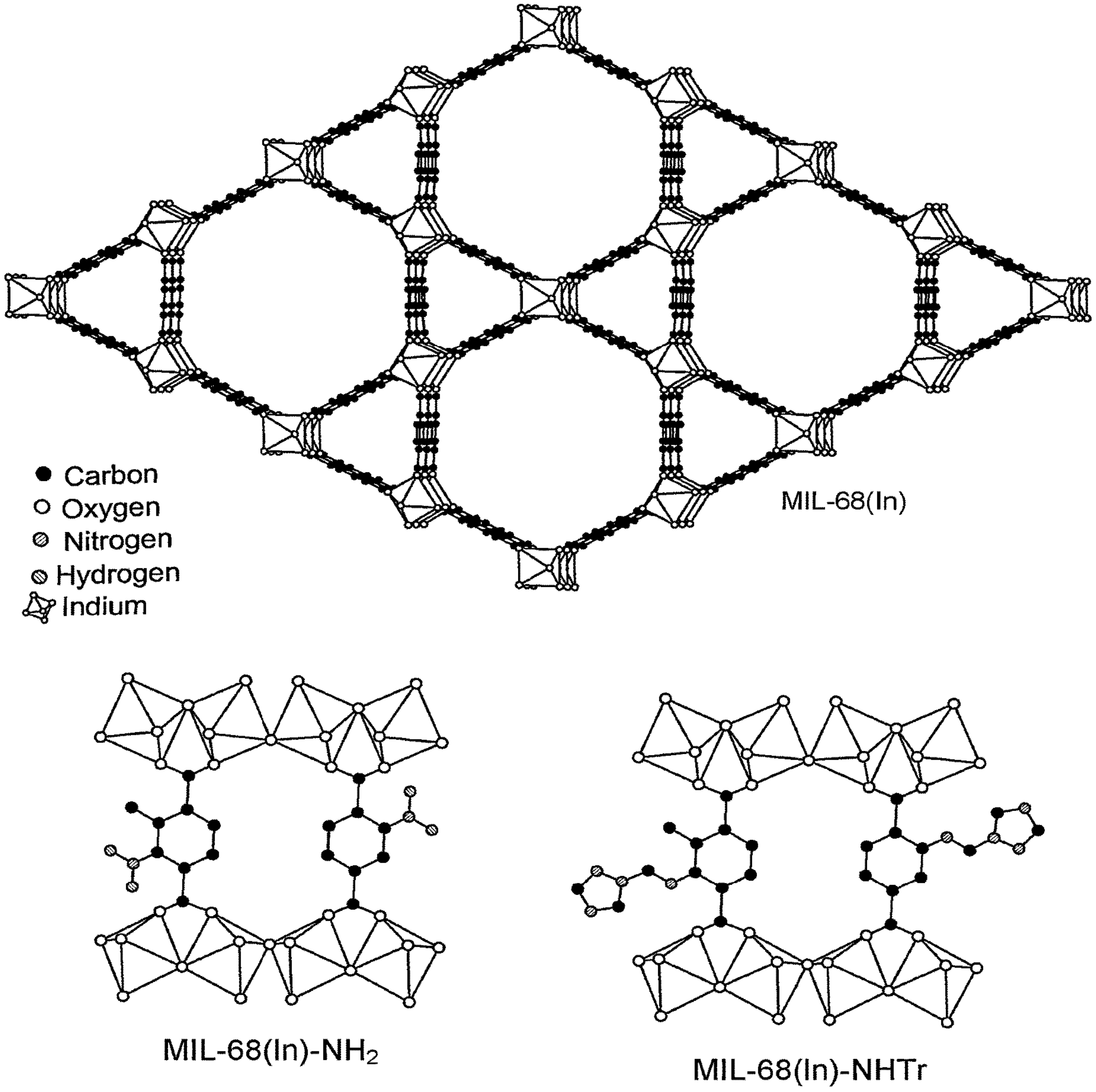
FIG. 2 is a schematic representation of MIL-68(In), MIL-68(In)—$NH_2$, MIL-68(In)—NHTr, according to embodiments of the present disclosure.

The reusability and non-leaching properties make the In-MOFs environmentally favorable catalysts. Moreover, In-MOFs can easily accept electrons in readily accessible high-level p-orbitals and act as a strong Lewis acid. MOFs are often functionalized with N-heterocyclic functional groups such as pyridine, imidazole, or triazole to provide Lewis basic sites (LBS) that increase the interaction with $CO_2$, thus enhancing $CO_2$ capture. However, functionalization with the N-heterocycles should always take place on the framework of the MOF to avoid undesirable coordination with metal nodes. Thus, in the present disclosure, the isoreticular synthesis of amine-functionalized MIL-68(In)—$NH_2$ and triazole-functionalized MIL-68(In)—NHTr are employed as bifunctional catalysts containing Lewis acid and basic sites for the capture of carbon dioxide and synergistically catalyzes a three-component cycloaddition of epoxides, primary aromatic amines, and $CO_2$ for the synthesis of oxazolidinones (FIG. 2).

Instrumentation $^1H$ and $^{13}C$ NMR spectra were recorded on a Bruker AM-400 spectrometer (manufactured by Bruker, 40 Manning Rd-Billerica, MA. United States) using $Me_4Si$ as the internal standard.

Elemental microanalyses (EA) were performed using a PerkinElmer-EA 2400 elemental analyzer (manufactured by PerkinElmer, 940 Winter Street Waltham, MA 02451 U.S.A). Powdered X-ray diffraction (PXRD) patterns of the samples were recorded using a Rigaku MiniFlex diffractometer, which was equipped with Cu-Kα radiation (manufactured by Rigaku, 3-9-12 Matsubara-cho, Akishima-shi, Tokyo, 196-8666, Japan). The data were acquired over the 2θ ranges of 5° and 30°. Fourier Transform Infrared (FTIR) spectra of MIL-68(In)—NHTr were obtained using a Nicolet 6700 Thermo Scientific instrument in the range of 400-4000 reciprocal centimeters ($cm^{-1}$), using KBr (manufactured by ThermoFisher Scientific, 168 Third Avenue. Waltham, MA USA 02451). Thermogravimetric analysis (TGA) of the samples was performed using a TA Q500. In the present disclosure, an activated sample of MIL-68(In)—NHTr (10 milligrams (mg)) was heated in an alumina pan under airflow (60 milliliter per minute (mL $min^{-1}$)) with a gradient of 10 degree Celsius per minute (° C. $min^{-1}$) in the temperature range of 30-800° C. Brunauer-Emmett-Teller (BET) surface areas of the MOFs were calculated by using the Micromeritics 3flex Adsorption Analyzer instrument (manufactured by Mircometrics Internation Corporation, 4356 Communications Dr. Norcross, GA 30093-2901, U.S.A). Total $CO_2$ captured by the prepared MOF samples was analyzed by Autosorb (Quant chrome, London, Ground Floor, 20, 22 Wenlock Rd, United Kingdom). In a typical procedure, 100 mg of a sample was taken in a long bulb tube, degassed at 120° C. (ramp 5° C./min) for 10 hours. After cooling down the temperature to the desired adsorption temperature, subsequent doses of $CO_2$ were injected. The instrument recorded each point of equilibrium up to 760 torr. The controlled vacuum was used to degas the sample for the next run. A plot was recorded based on the adsorption and desorption of $CO_2$ versus pressure. The surface morphology of these materials was discerned using a field emission scanning electron microscope (FESEM, LYRA 3 Dual Beam, Tescan, 21 623 00 Brno-Kohoutovice Czech Republic), which operated at 30 kilovolts (kV). The FESEM samples were prepared from suspension in ethanol. The surface chemical analyses were performed using an X-ray photoelectric emission spectroscopy (XPS) system equipped with an Al—Kα micro-focusing X-ray monochromator (ESCALAB 250Xi XPSMicroprobe, ThermoFisher Scientific, 168 Third Avenue. Waltham, MA USA 02451). Temperature-programmed desorption (TPD) profiles of $CO_2$ from the MIL-68(In)—NHTr were conducted on an AutoChem 2920 equipped with a thermal conductivity detector (TCD) detector. A sample of 100 mg was pretreated in Argon (Ar) at 373 kelvin (K) for 2 hours. After being cooled to 323 K, the sample was exposed to $CO_2$ (99.99%) for 60 minutes, flushed with Ar at 373 K to remove physically adsorbed $CO_2$, and then cooled to 323 K. $CO_2$-TPD was measured from 300 K to 600 K in an Ar flow at a rate of 5° C./min. Temperature-programmed desorption (TPD) profiles of $NH_3$ from the MIL-68(In)—NHTr were conducted on an AutoChem 220 (manufactured by Mircometrics Internation Corporation, 4356 Communications Dr. Norcross, GA 30093-2901, U.S.A) equipped with a TCD detector. A sample of 50 mg was pretreated in Ar at 373 K for 2 hours. After cooling to 323 K, the sample was exposed to 1.01% $NH_3$/Ar for 30 minutes, flushed with Ar at 373 K to remove physically adsorbed ammonia, and then cooled to 323 K. $NH_3$-TPD was measured from 60° C. to 350° C. in a Ar flow at a rate of 5° C./min.

Procedure for $CO_2$ Cycloaddition

Completely dried MIL-68(In)—NHTr material (2.0 mol %), n-tetrabutylammonium bromide (TBABr, 1.0 mol %), and epoxide (10.0 mmol) were added to a 50 mL size Schlenk tube at room temperature. 1 bar of $CO_2$ was introduced using a balloon to form a reaction mixture and the reaction mixture was allowed to stir at 50° C. for 6 hours. The reaction was monitored by TLC.

After completion of the reaction, the mixture was cooled to room temperature. The reaction mixture was then diluted with chloroform and centrifuged to separate the catalysts. The organic layer was concentrated and passed through a short silica column and eluted with an ethyl acetate/hexane mixture. The pure form of the respective cyclic carbonates was dried yield was checked and taken for analysis by $^1$H NMR and $^{13}$CNMR Selectivity The selectivity of the products was analyzed using $^1$H NMR spectroscopy of the product without any purification, based on the integration of the $CH_2Cl$ signals of chloropropylene carbonate.

Leaching Test

The leaching test was performed by the hot filtration method. During this test, the catalytically active particles were removed after 3 hours from the reaction by filtration through a hot frit, and the filtrate was monitored for continued activity. It was found that the reaction did not proceed, supporting that no catalytically active metals leached from the MIL-68(In)—NHTr into the filtrate.

Reusability Test

To reuse the catalysts MIL-68(In)—NHTr after completion of the reaction, the reaction mixture was diluted with chloroform, and the catalysts were recovered by simple centrifugation (5000 rotations per minute (rpm)). Recovered MIL-68(In)—NHTr was washed three times with 10 mL of methanol to remove any remaining epoxides and TBABr, and dried under vacuum at 100° C. overnight. The subsequent reaction conditions for the repeated test were kept the same as the reaction conditions used in the first reaction.

Synthesis

Synthesis of the Linker

Scheme 1. Synthesis of the linker $H_2L$.

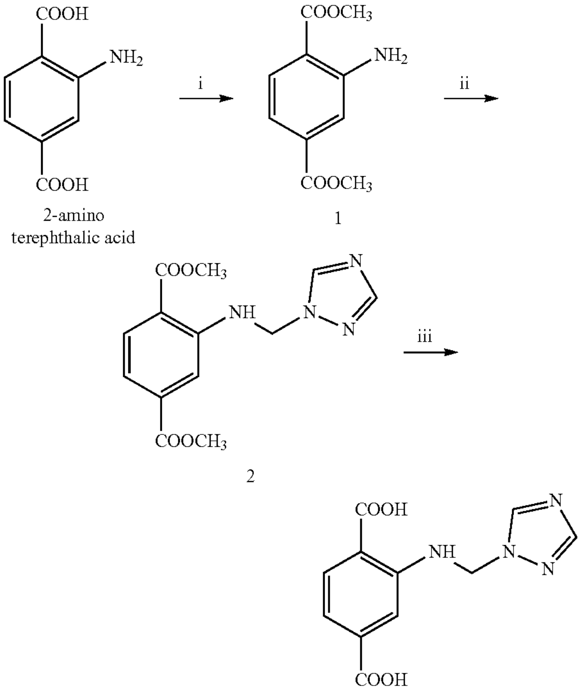

2-amino terephthalic acid

1

2

$H_2L$

Reagents and conditions: (i) MeOH, HCl (4 drops), reflux, 10 h; (ii) $CH_2O$ solution, EtOH:$H_2O$ (1:3), 1,2,4-Triazole, r.t, 24 h; (iii) EtOH, KOH, reflux, 12 h.

Synthesis of Compound 2 (dimethyl 2-(((1H-1,2,4-triazol-1-yl)methyl)amino)terephthalate)

Figure 3:
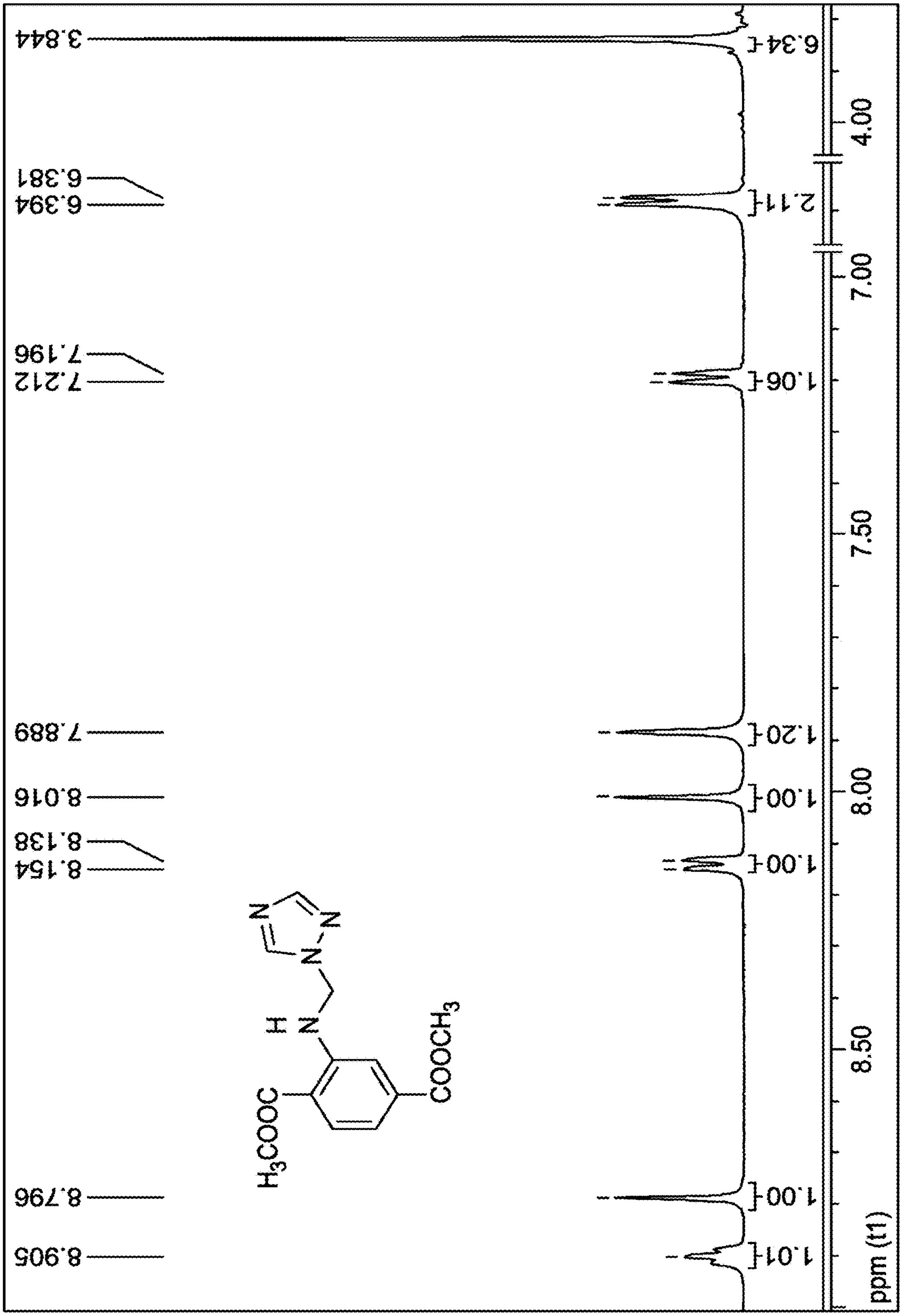
FIG. 3 is a proton ($^1$H) nuclear magnetic resonance (NMR) spectrum of dimethyl 2-(((1H-1,2,4-triazol-1-yl) methyl)amino)terephthalate, according to embodiments of the present disclosure.
Figure 4:
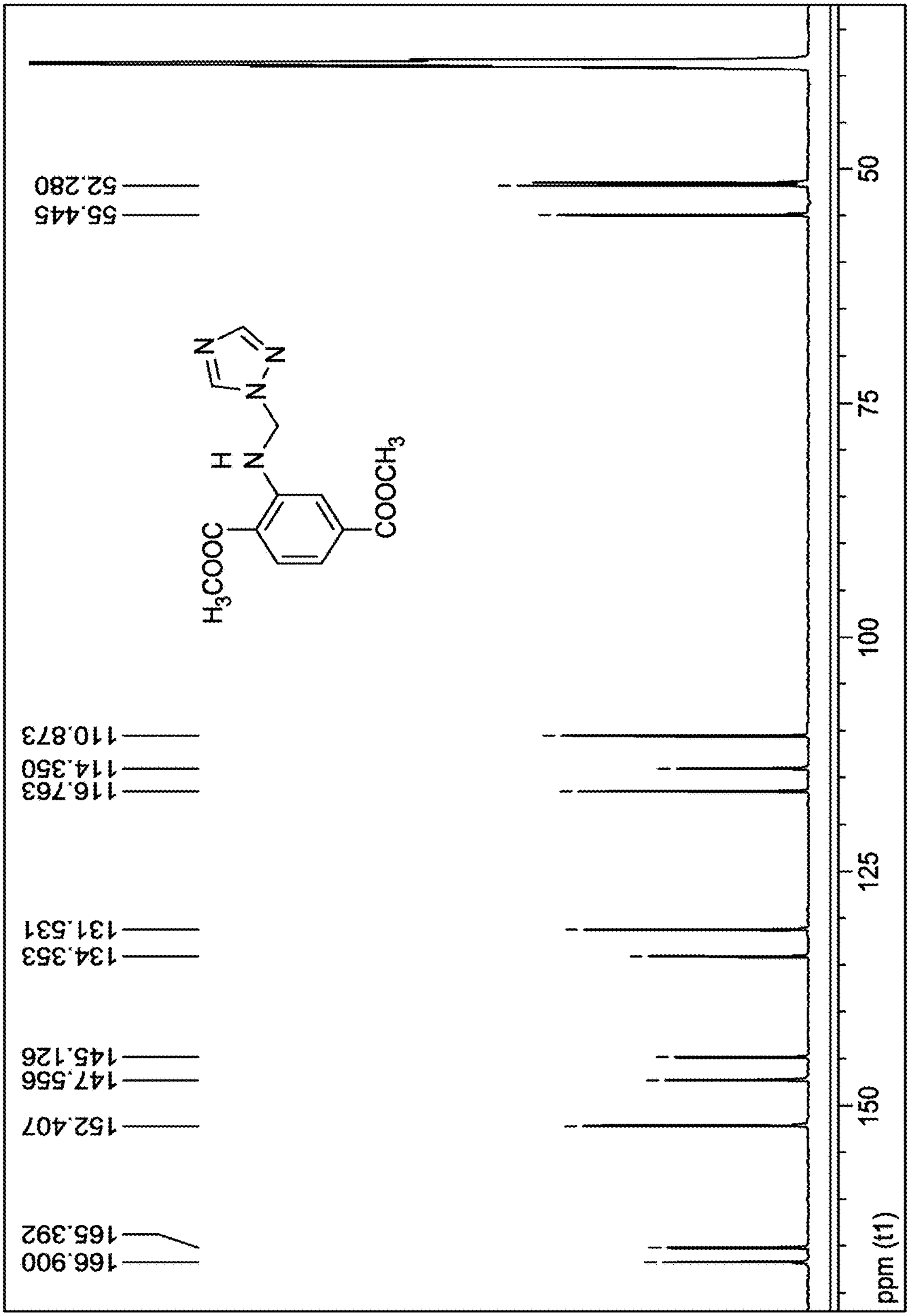
FIG. 4 is a carbon-13 ($^{13}$C) NMR spectrum of dimethyl 2-(((1H-1,2,4-triazol-1-yl)methyl)amino)terephthalate, according to embodiments of the present disclosure.

A solution of 2-aminoterephthalic acid (1.000 g, 5.6 millimoles (mmol)) in methanol (20 mL) and 4 drops of HCl was refluxed for 10 hours. The solvent was removed under vacuum and the residue was diluted with water and extracted with $CH_2Cl_2$. The organic layer was dried over anhydrous $Na_2SO_4$ and concentrated. The residue was purified by $SiO_2$ column chromatography (elution with 1:3 EtOAc:hexane) to give 1 in 90% yield. A mixture of 1 (900 mg, 4.4 mmol), 1,2,4-triazole (305 mg, 4.4 mmol), formaldehyde (37%) (130 mg, 4.4 mmol) in 20 mL of 1:3 ethanol:water was stirred for 24 hours. The solvent was removed under vacuum and the residue was diluted with water and extracted with ethyl acetate. The organic layer was dried over anhydrous $Na_2SO_4$ and concentrated. The residue was purified by $SiO_2$ column chromatography (elution with 1:2 EtOAc:hexane) to give compound 2 in 65% yield. $^1$H NMR (DMSO-$d_6$) δ 3.84 (s, 6H), 6.39 (d, J=5.2 Hz, 2H), 7.20 (d, J=6.4 Hz, 1H), 7.89 (s, 1H), 8.02 (s, 1H), 8.14 (d, J=6.4 Hz, 1H), 8.79 (s, 1H), 8.91 (bs, 1H, NH); $^{13}$C NMR (DMSO-$d_6$) δ 55.44, 110.87, 114.35, 116.76, 131.53, 134.35, 145.13, 147.56, 152.41, 165.39, 166.9; Anal. Calcd for $C_{13}H_{14}N_4O_4$: C, 53.79; H, 4.86; N, 19.30; Found: C, 53.88; H, 4.91; N, 19.41 (FIGS. 3-4).

Figure 5:
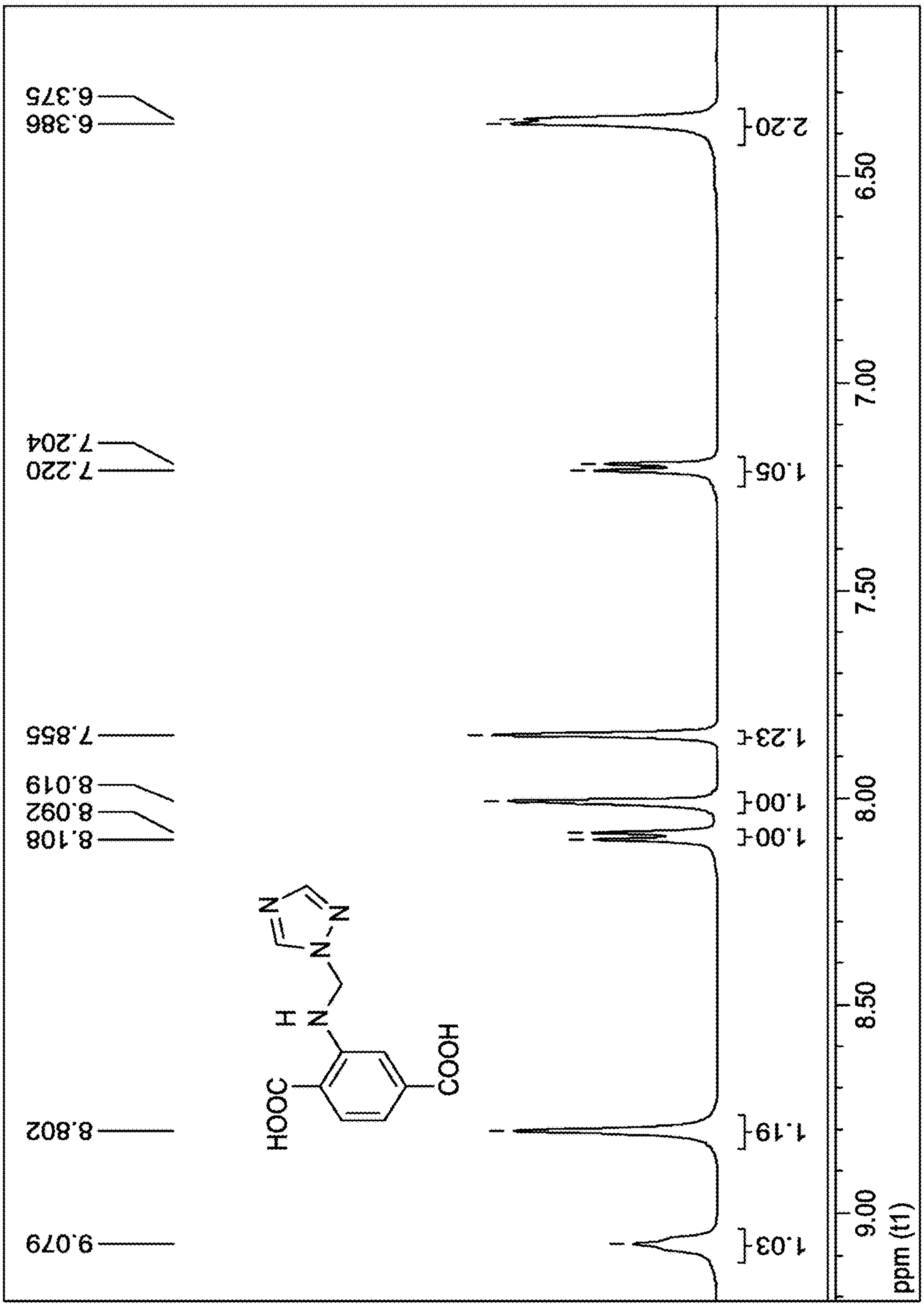
FIG. 5 is a $^1$H NMR spectrum of 2-(((1H-1,2,4-triazol-1-yl)methyl)amino)terephthalic acid ($H_2L$), according to embodiments of the present disclosure.
Figure 6:
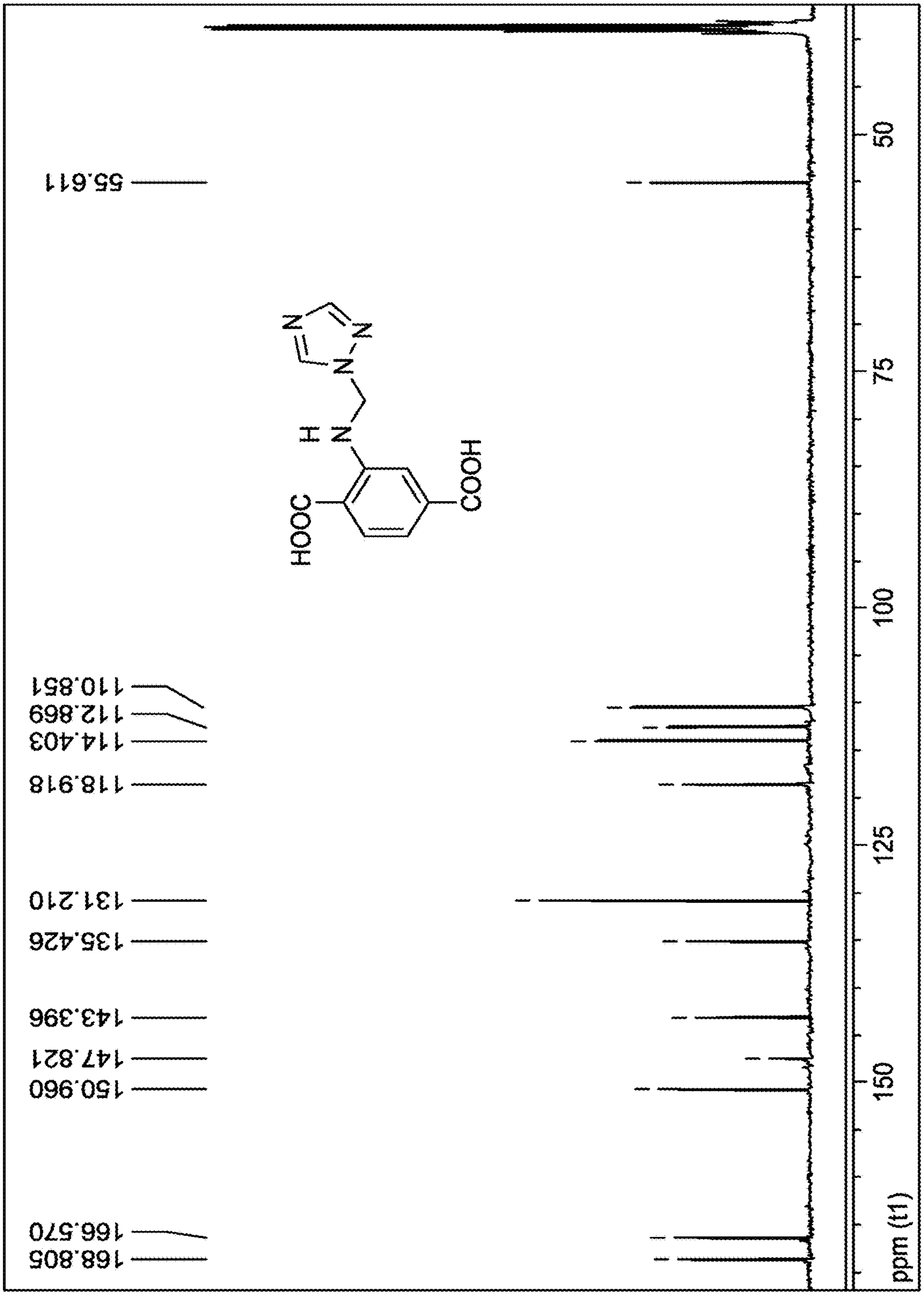
FIG. 6 is a $^{13}$C NMR spectrum of the 2-(((1H-1,2,4-triazol-1-yl)methyl)amino)terephthalic acid ($H_2L$), according to embodiments of the present disclosure.

Synthesis of $H_2L$ linker, 2-((1H-1,2,4-triazol-1-yl)methylamino)terephthalic acid Compound 2 (600 mg, 2.1 mmol) was refluxed with an ethanolic solution of KOH for 12 hours. The solvent was removed under vacuum and the remaining residue was diluted with water and the pH was adjusted to 5.0 by the addition of HCl (1 M). The off-white solid precipitated was filtered with a Buchner base washed with water and recrystallized from ethanol to give linker $H_2L$ in 89% yield. $^1H$ NMR (DMSO-$d_6$) δ 6.38 (d, J=4.4 Hz, 2H), 7.21 (d, J=6.4 Hz, 1H), 7.86 (s, 1H), 8.02 (s, 1H), 8.1 (d, J=6.4 Hz, 1H), 8.8 (s, 1H), 9.08 (bs, 1H, NH); $^{13}C$ NMR (DMSO-$d_6$) δ 55.61, 110.85, 112.87, 114.40, 118.92, 131.21, 135.43, 143.39, 147.82, 150.96, 166.57, 168.81; Anal. Calcd for $C_{11}H_{10}N_4O_4$: C, 50.38; H, 3.84; N, 21.37; Found: C, 50.47; H, 3.96; N, 21.44 (FIGS. 5-6).

Synthesis of MIL-68(In)—$NH_2$

MIL-68(In)—$NH_2$ was synthesized by a slight modification of the method reported in the literature [Volkringer C, Meddouri M, Loiseau T, Guillou N, Marrot J, Ferey G, Haouas M, Taulelle F, Audebrand N, Latroche M. (2008) Inorg Chem 47: 11892-11901, incorporated herein by reference in its entirety]. Indium nitrate (1.57 mmol, 612.3 mg) and 2-amino-1,4-benzenedicarboxylic acid (1.13 mmol, 204.7 mg) were dissolved in DMF (10 mL) with ultrasonic vibration for 10 minutes. The as-obtained mixture was transferred to a 20 mL vial and heated at 373 K for 48 hours. Then the vial was cooled in the air to room temperature. The resulting MIL-68(In)—$NH_2$ was washed with DMF (5-10 mL) and centrifuged (10,000 rpm for 30 min) three times, and then sequentially immersed in methanol (5-10 mL three times per day) for three 24 hour periods. Finally, MIL-68(In)—$NH_2$ was activated by removing the solvent under vacuum for 24 hours at 100° C. The yield was 67% based on indium. FTIR (KBr, $cm^{-1}$): 3426, 1658, 1560, 1433, 1384, 1253, 1098, 769, 671. Anal. Calcd for $C_{11}H_{17}N_2O_8In$ (In(OH)(2-$NH_2$BDC)(DMF)($H_2O$)$_2$): C, 31.45; H, 4.08; N, 6.67; Found: C, 31.53; H, 4.14; N, 6.75.

Synthesis of MIL-68(In)—NHTr

MIL-68(In)—NHTr was synthesized similarly as above by dissolving indium nitrate (1.57 mmol, 612.3 mg) and $H_2L$ (1.13 mmol, 296.0 mg) in DMF (20 mL) with ultrasonic vibration for 10 minutes. The as-obtained mixture was transferred to a 20 mL vial and heated at 373 K for 48 hours. Then the vial was cooled in the air to room temperature. The resulting MIL-68(In)—NHTr was washed, in the same way as the previous method, three times with DMF (5-10 mL) using a centrifuge (10,000 rpm for 30 min), and then sequentially immersed in methanol (5-10 mL three times per day) for three 24 hour periods. Finally, MIL-68(In)—NHTr was activated by removing the solvent under vacuum for 24 hours at 100° C. The yield was 53% based on indium. FTIR (KBr, $cm^{-1}$): 3442, 1697, 1613, 1559, 1505, 1390, 1295, 1156, 1026, 881, 821, 746, 541. Anal. Calcd for $C_{14}H_{20}N_5O_8In$ (In(OH)(2-$TrCH_2NHBDC$)(DMF)($H_2O$)$_2$): C, 33.55; H, 4.02; N, 13.97; Found: C, 33.66; H, 4.11; N, 14.03.

Characterization of Linker $H_2L$

The present disclosure involves the functionalization of 2-aminoterephthalic acid with a 1,2,4-triazole moiety to produce linker $H_2L$ (Scheme 1). Dimethyl 2-aminoterephthalate (compound 1), formaldehyde, and 1,2,4-triazole were coupled together to give compound 2, and subsequent deprotection of 2 by alkaline hydrolysis gave $H_2L$ in efficient yield (Scheme 1). The structures of 2 and $H_2L$ were corroborated by $^1H$ NMR, $^{13}C$ NMR, and elemental analysis data (FIGS. 3-6). The $^1H$ NMR spectra of $H_2L$ exhibited a doublet peak at δ 6.38 parts per million (ppm), which corresponds to the (—$CH_2$—) protons bridging the 2-aminoterephthalic acid with 1,2,4-triazole. Furthermore, singlet peaks at δ 8.8 ppm and 8.02 ppm are assigned to the protons of the triazole ring, while the doublet peaks at δ 8.09 ppm, δ 7.21 ppm, and the singlet peak at δ 7.85 ppm correspond to the benzene ring protons of terephthalate.

Characterization of MIL-68(In)—$NH_2$ and MIL-68(In)—NHTr

Figure 7:
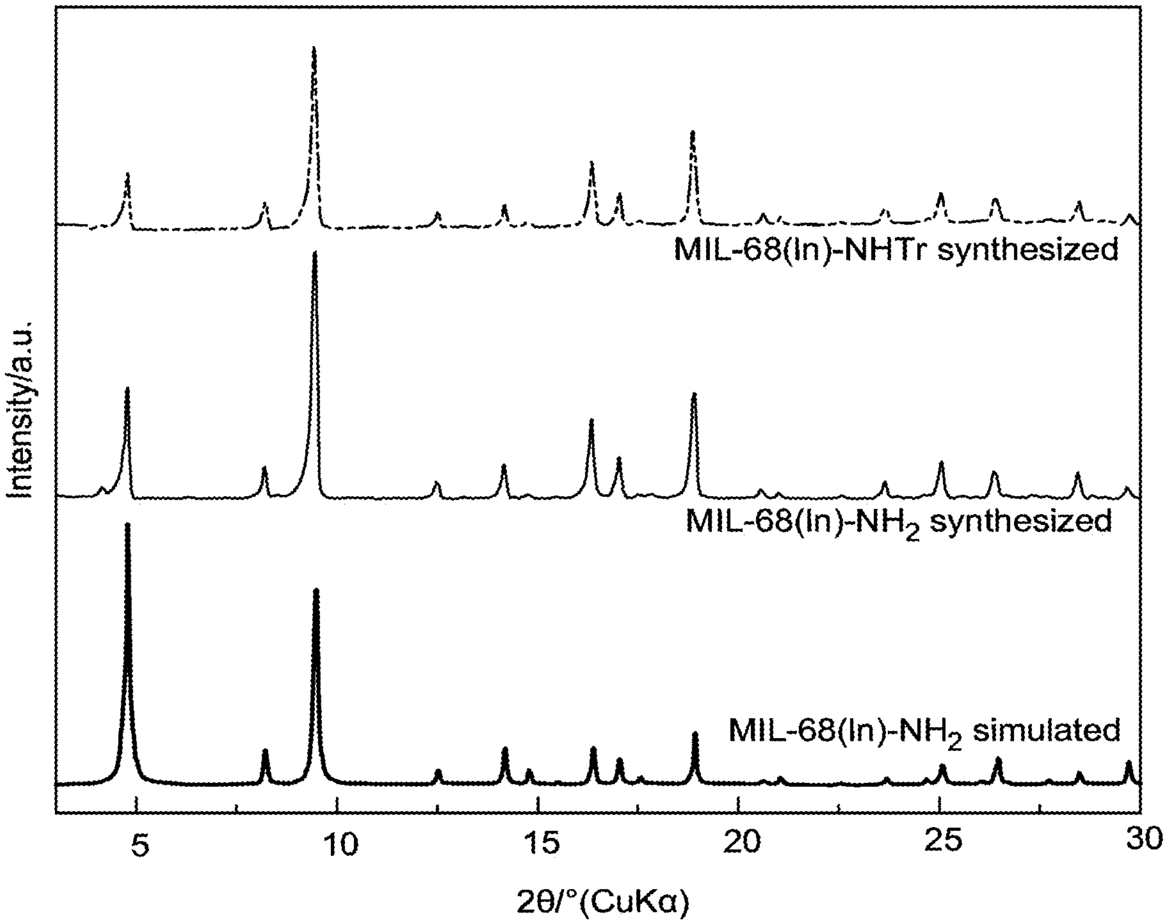
FIG. 7 depicts powder X-ray diffraction (PXRD) analysis of the MIL-68(In)—NHTr synthesized, MIL-68(In)—$NH_2$ synthesized, and MIL-68(In)—$NH_2$ simulated, according to embodiments of the present disclosure.
Figure 8:
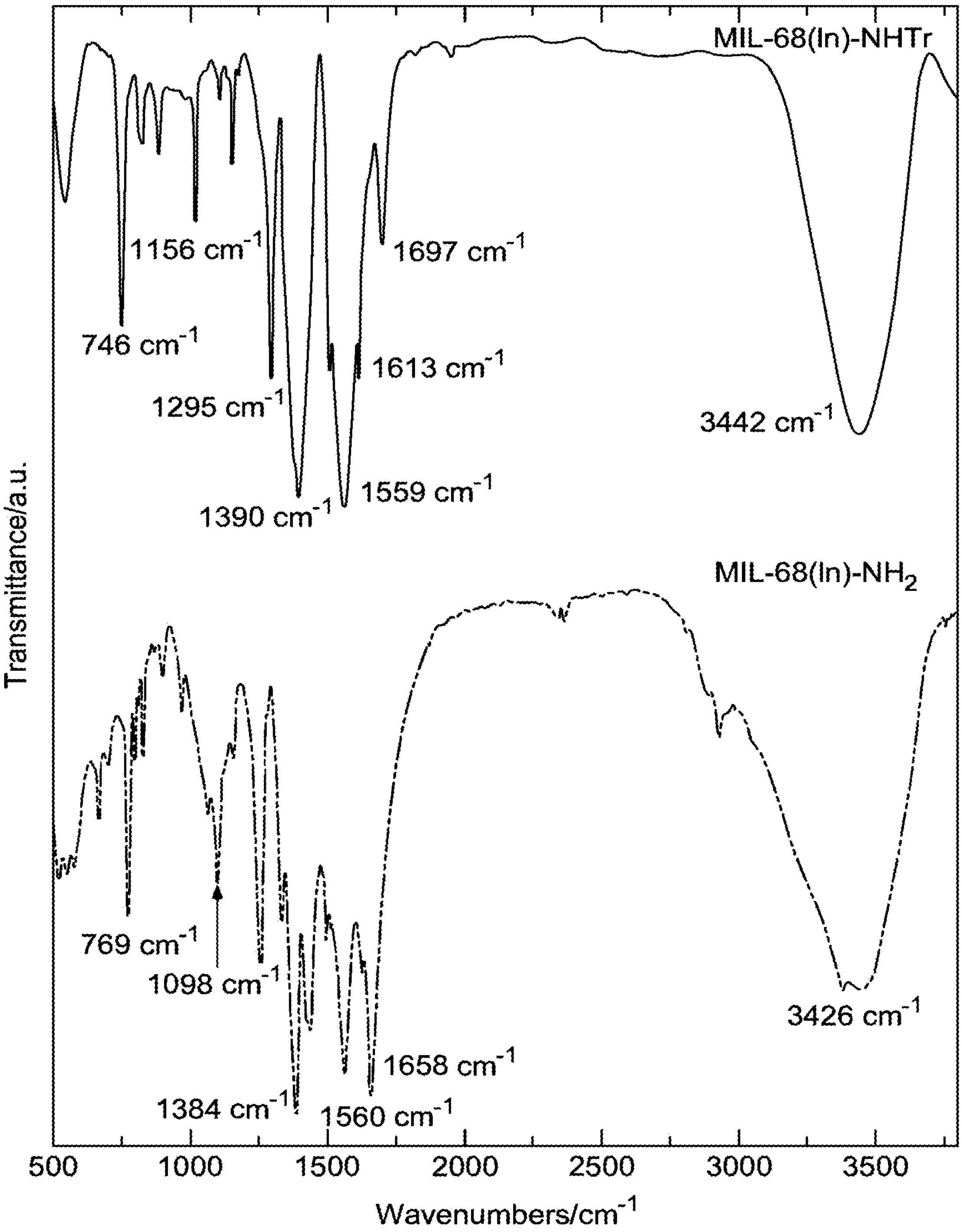
FIG. 8 depicts Fourier transform infrared (FTIR) spectrum of the MIL-68(In)—NHTr and MIL-68(In)—$NH_2$, according to embodiments of the present disclosure.
Figure 9:
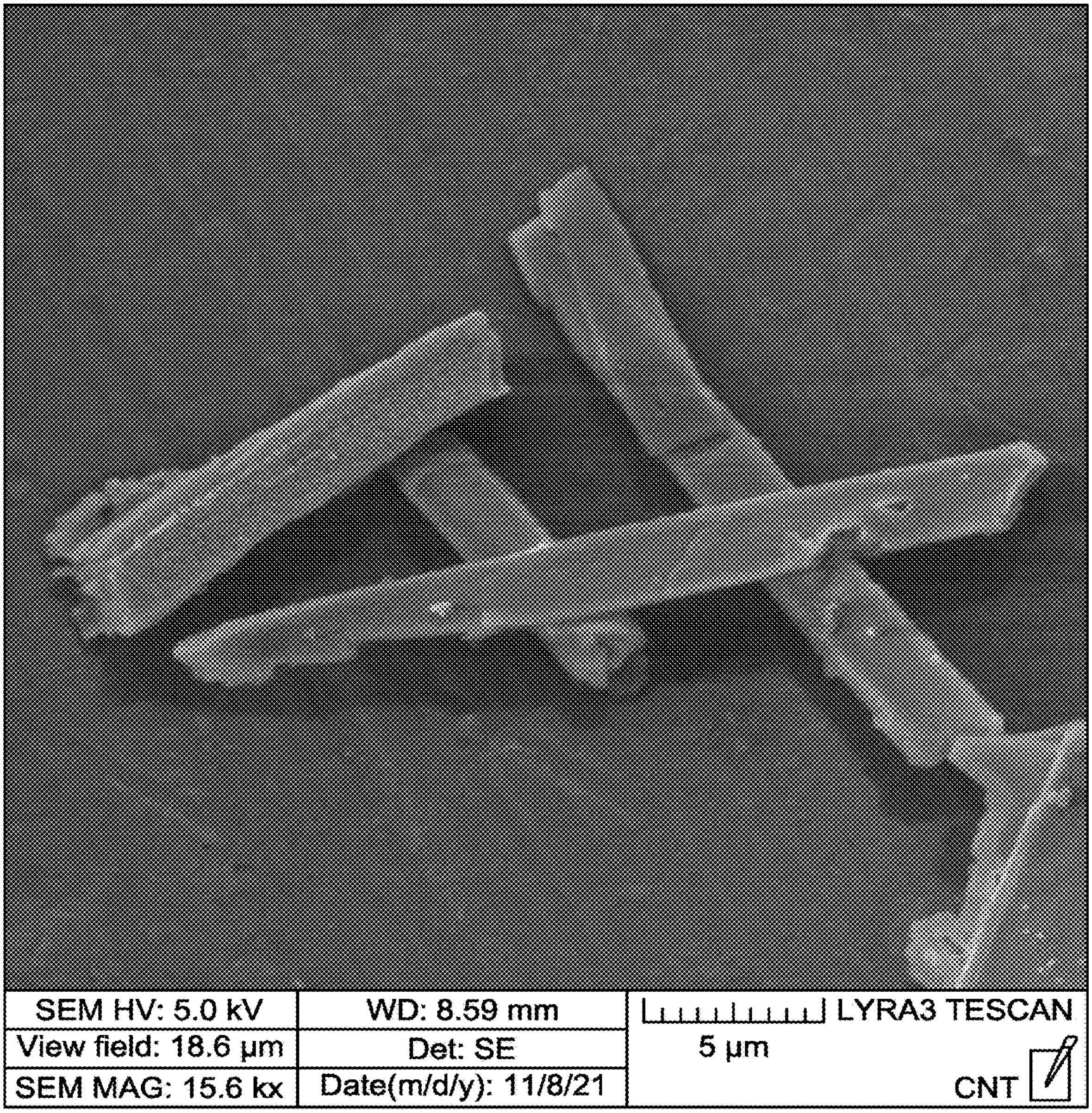
FIG. 9 depicts scanning electron microscope (SEM) image of the MIL-68(In)—NHTr, according to embodiments of the present disclosure.

MIL-68(In)—$NH_2$ and MIL-68(In)—NHTr were prepared by a slight modification of the literature procedure [Volkringer C, Meddouri M, Loiseau T, Guillou N, Marrot J, Ferey G, Haouas M, Taulelle F, Audebrand N, Latroche M. (2008) Inorg Chem 47: 11892-11901, incorporated herein by reference in its entirety] as described above. Powder X-Ray Diffraction (PXRD) of MIL-68(In)—$NH_2$ exhibited characteristic peaks at 2θ=4.78°, 8.2°, 9.48°, and 12.52°. These distinctive peaks were also present in the triazole-functionalized MIL-68(In)—NHTr (FIG. 7), which demonstrates appending the triazole moiety to a main backbone of MIL-68(In)—$NH_2$ does not disturb the framework connectivity and the crystallinity of the MOF is intact. The study of the FTIR spectrum of MIL-68(In)—NHTr and MIL-68(In)—$NH_2$ (FIG. 8) exhibited a broad band centered at 3442 $cm^{-1}$ and 3426 $cm^{-1}$, respectively, due to the O—H stretching vibrations of the coordinated water molecules and the N—H stretching vibrations. Peaks at 1697 $cm^{-1}$, 1658 $cm^{-1}$, and 1559 $cm^{-1}$, 1560 $cm^{-1}$ correspond to asymmetric and symmetric stretching of the coordinated carboxylated groups (COO—) of MIL-68(In)—NHTr and MIL-68(In)—$NH_2$. Sharp peaks at 1390 $cm^{-1}$ and 1342 $cm^{-1}$ are assigned to the C—N stretching vibrations of the amine and the benzene ring in MIL-68(In)—NHTr and MIL-68(In)—$NH_2$, respectively. Other sharp peaks at 1384 $cm^{-1}$ in both the MOFs represent the C═C stretching vibration of the benzene ring. Peaks at 746 $cm^{-1}$ and 769 $cm^{-1}$ are due to the stretching vibration of the C—H bond of the benzene ring of the framework of MIL-68(In)—NHTr and MIL-68(In)—$NH_2$, respectively. In MIL-68(In)—NHTr, additional peaks from the appended triazole ring are the C═N stretching peak at 1613 $cm^{-1}$, C—N stretching peak at 1505 $cm^{-1}$ and 1295 $cm^{-1}$, and N—N stretching peak at 1156 $cm^{-1}$. Field emission scanning electron microscopy (FESEM) image of the microcrystalline MIL-68(In)—NHTr shows evenly distributed rod-shaped cuboid formations (FIG. 9). The MIL-68(In)—NHTr formations are 5 to 50 micrometers (μm), preferably 5 to 30 μm, and more preferably 5 to 20 μm in length.

Figure 10:
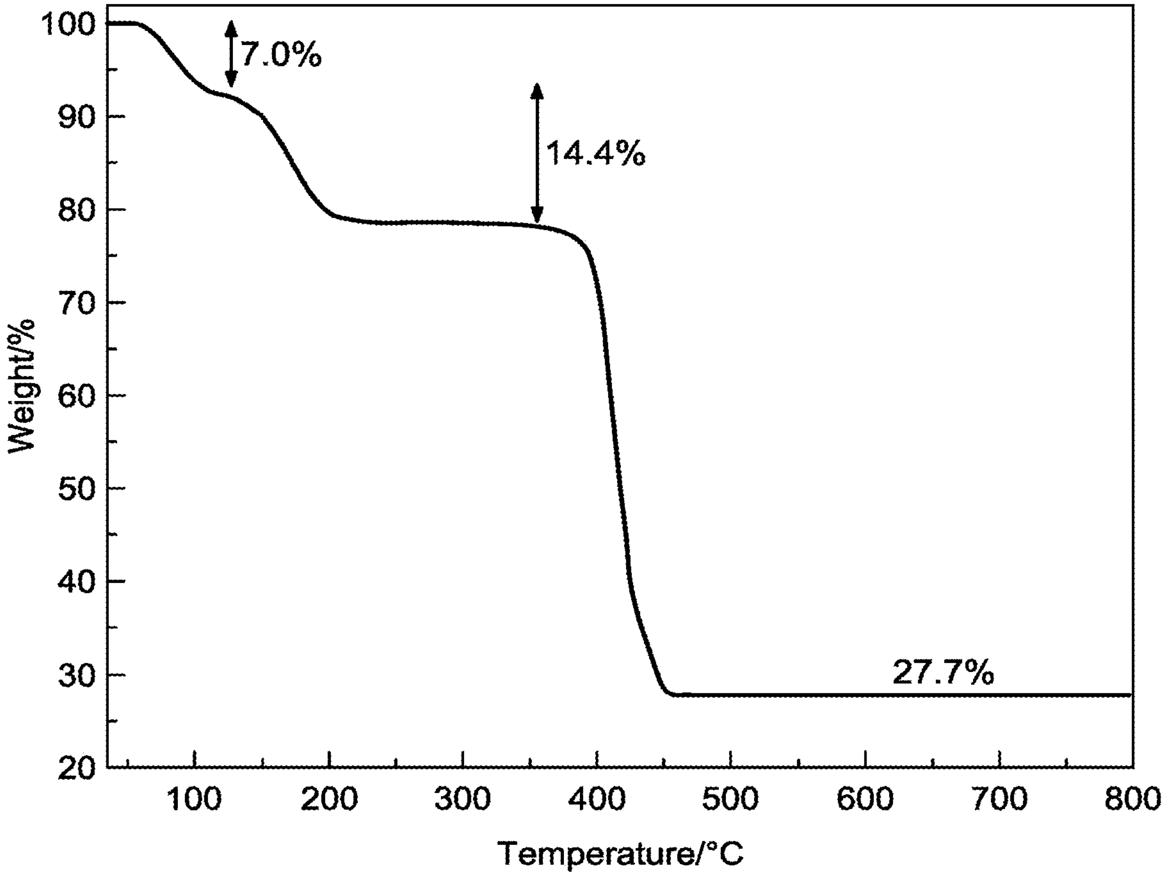
FIG. 10 depicts thermogravimetric analysis (TGA) of the MIL-68(In)—NHTr, according to embodiments of the present disclosure.
Figure 11:
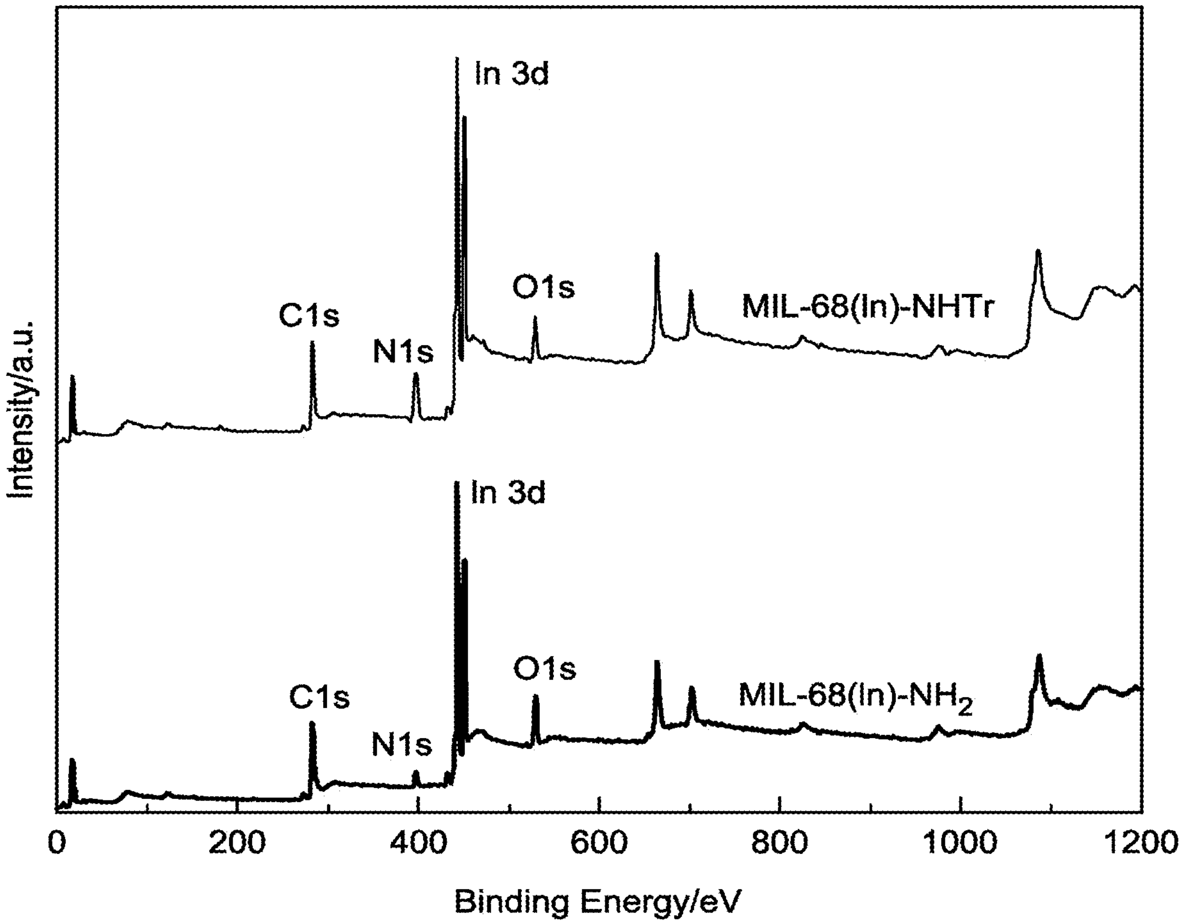
FIG. 11 depicts an X-ray photoelectric emission spectroscopy (XPS) analysis of MIL-68(In)—NHTr and MIL-68 (In)—$NH_2$, according to embodiments of the present disclosure.

Thermal stability of MIL-68(In)—NHTr was determined by the thermogravimetric analysis (TGA) with a heating rate of 5° C. $min^{-1}$ under air (FIG. 10). There is a preliminary weight loss of 7.0% within 100° C., due to the removal of water, and another mass loss of 14.4% at 200° C., due to the removal of trapped solvent molecules, N,N-Dimethylformamide (DMF), from the pores and attached to the framework of the MOF. Finally, there is an abrupt mass loss of 50.9% at 390° C. due to the decomposition of the MIL-68(In)—NHTr framework, with a remaining residue of 27.7% corresponding to $In_2O_3$. These results support that the triazole-functionalized MOF has good thermal stability up to 390° C. Comparative XPS studies of MIL-68(In)—NHTr and MIL- 68(In)—$NH_2$ were performed in FIG. 11. In both spectra, characteristic peaks of $In3d_{3/2}$ and $In3d_{5/2}$ at 451.0 electron volts (eV) and 443.9 eV, respectively, were found. Spectra of both the MOFs characteristic peaks at 284.1 eV and 531.9 eV are assigned to C1s and O1s, respectively. Furthermore, a peak at 398.0 eV is assigned to N1s, and in the case of MIL-68(In)—NHTr, the peak of N1s is broader and more intense than MIL-68(In). This supports the coupling of the triazole moiety with the metal-organic framework.

Figure 12:
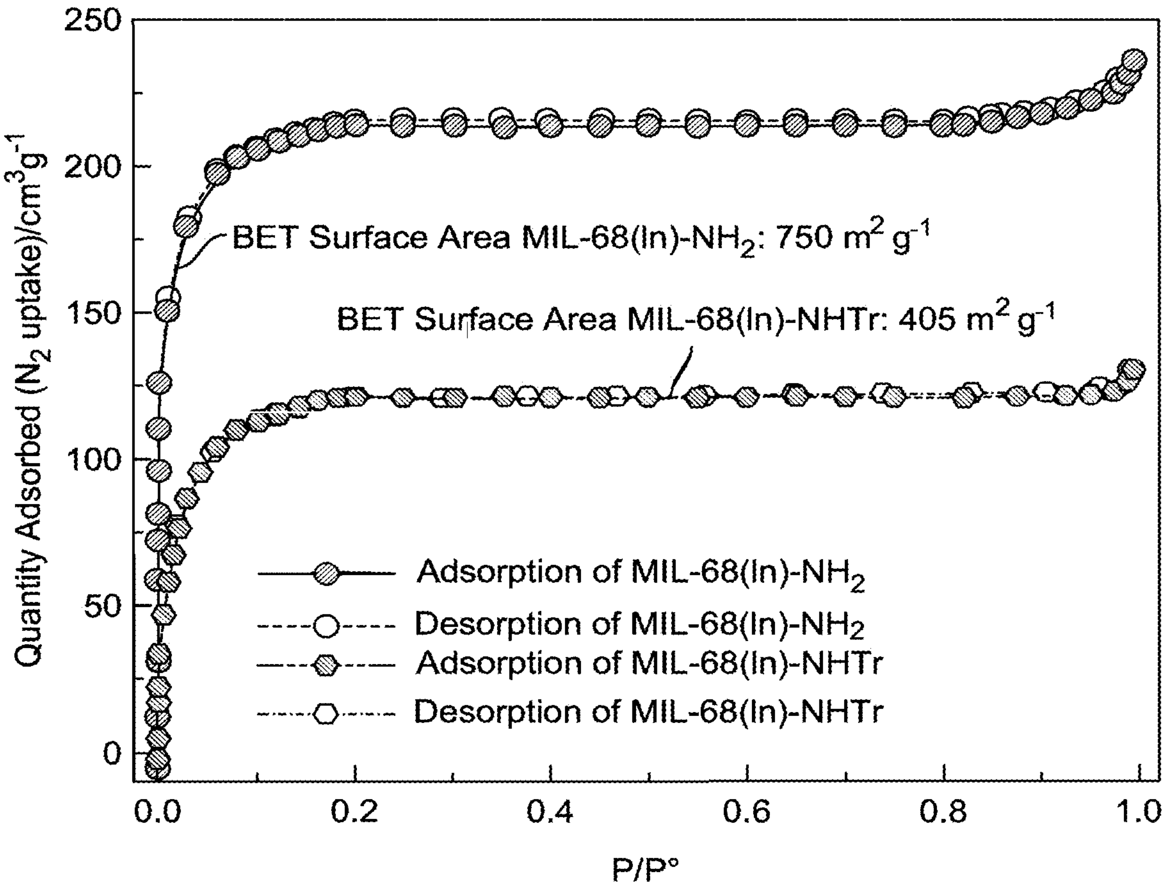
FIG. 12 depicts $N_2$ adsorption isotherm of the MIL-68 (In)—NHTr and MIL-68(In)—$NH_2$, according to embodiments of the present disclosure.
Figure 13:
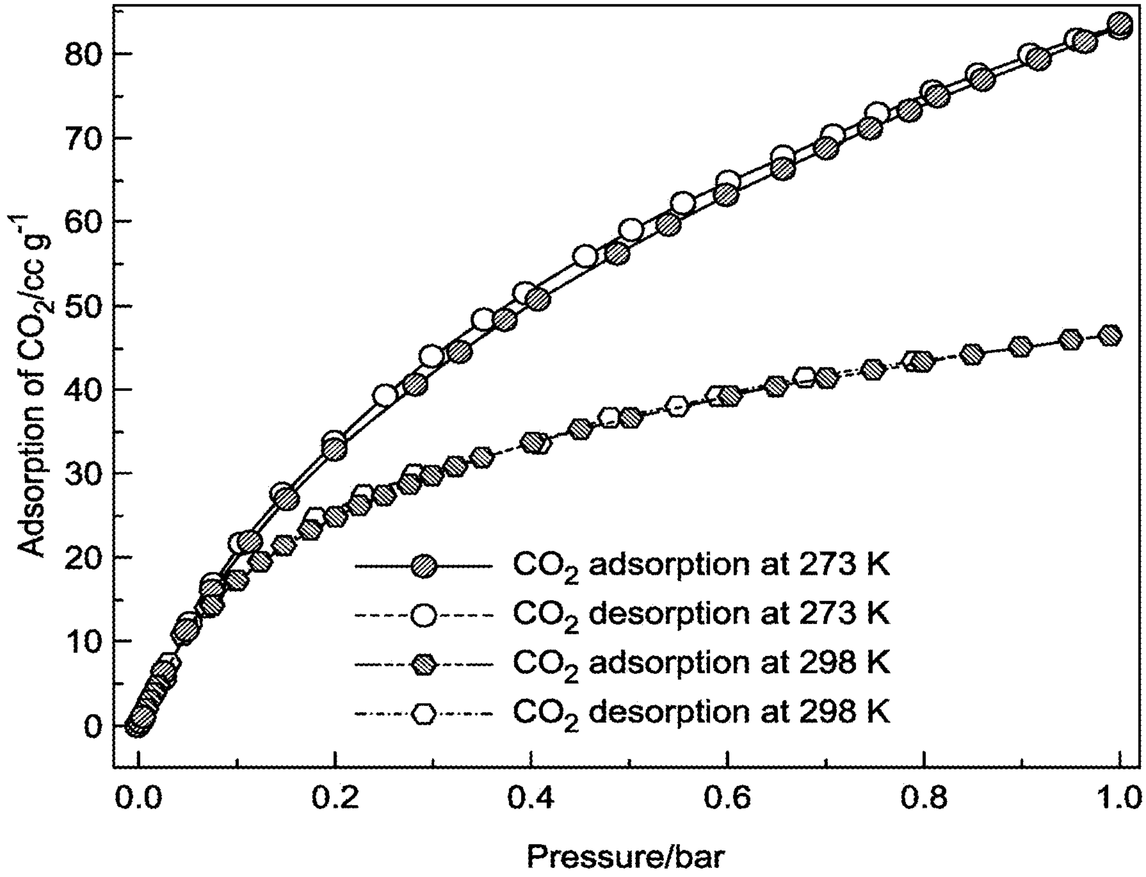
FIG. 13 depicts $CO_2$ adsorption isotherm of the MIL-68 (In)—NHTr, according to embodiments of the present disclosure.
Figure 14:
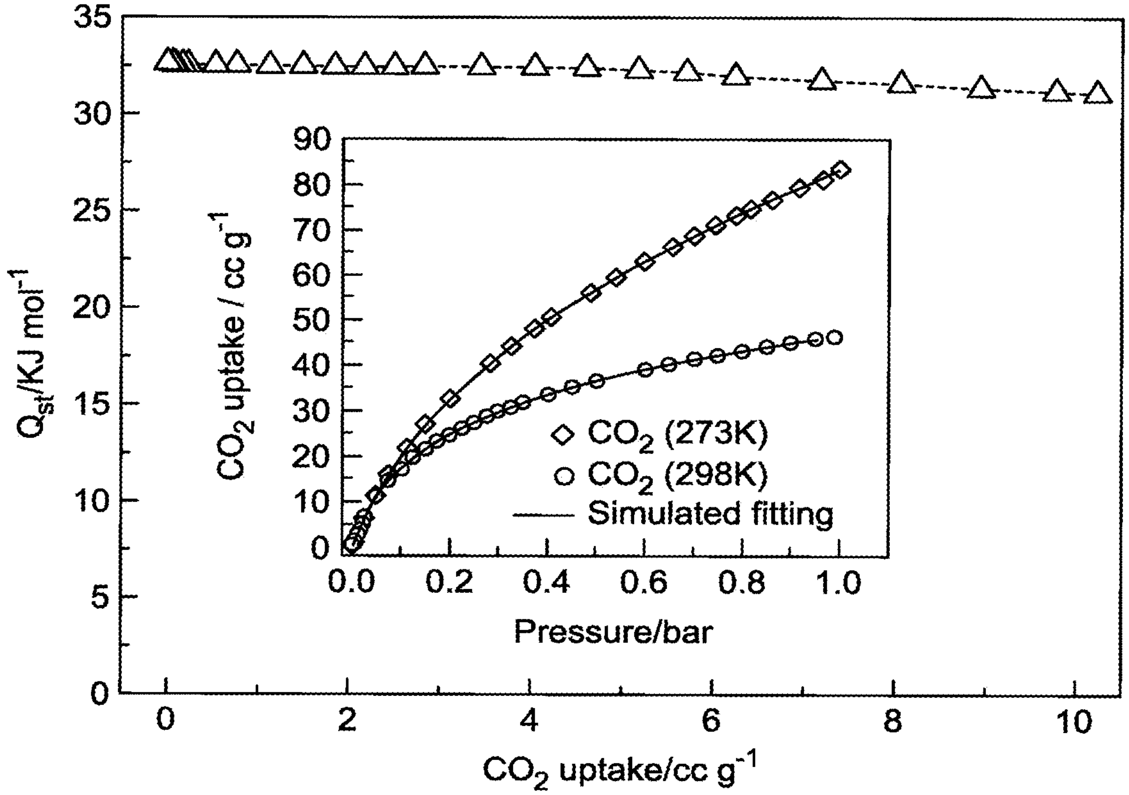
FIG. 14 depicts isosteric heat of adsorption ($Q_{st}$) calculation for the MIL-68(In)—NHTr, according to embodiments of the present disclosure.
Figure 15:
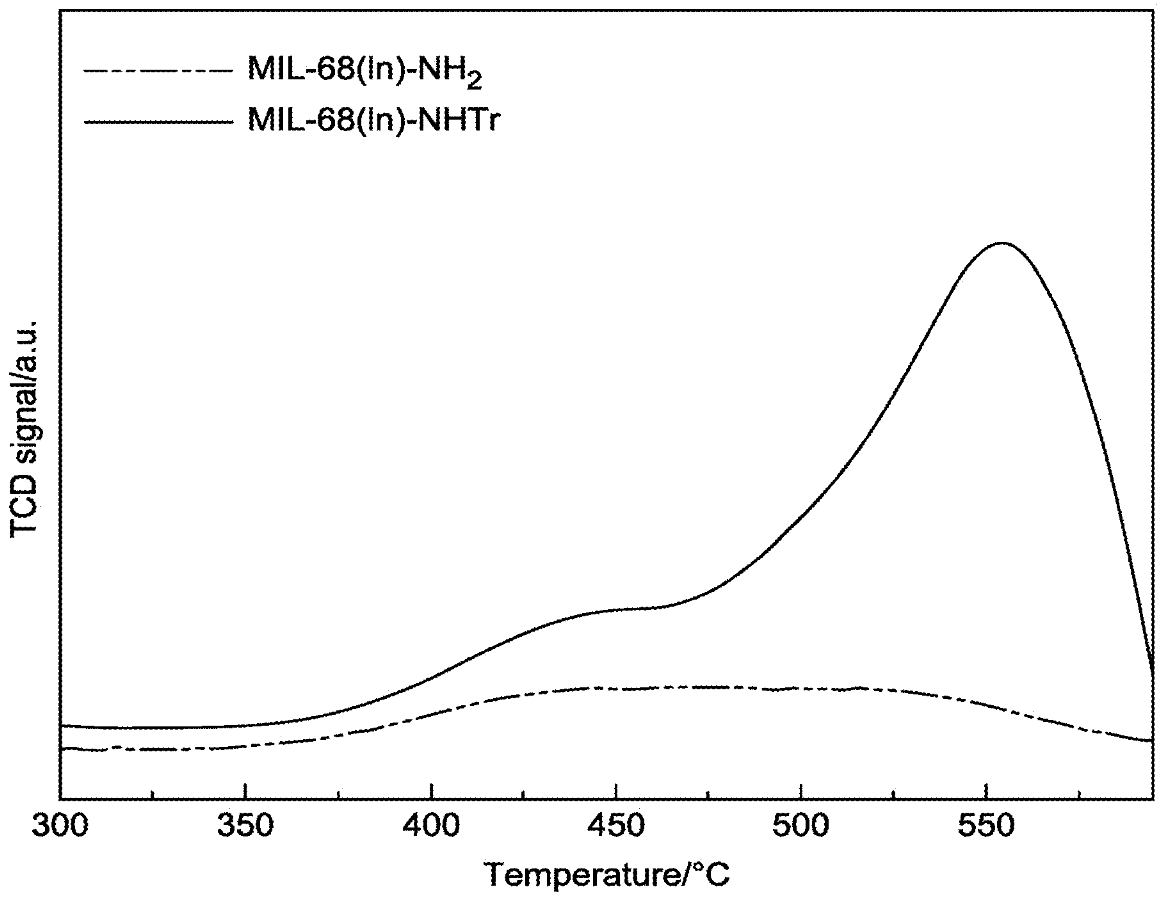
FIG. 15 depicts $CO_2$-temperature programmed desorption ($CO_2$-TPD) of the MIL-68(In)—NHTr and MIL-68(In)—$NH_2$, according to embodiments of the present disclosure.

Nitrogen physisorption isotherm of both MIL-68(In)—NHTr and MIL-68(In)—$NH_2$ indicated that it is Type I with a sharp uptake at a low relative pressure ($P/P^o$) of 0 to 0.05, which predicts that both metal-organic frameworks are microporous (FIG. 12). BET surface area obtained from the isotherms for MIL-68(In)—$NH_2$ was 750 meter square per gram ($m^2\ g^{-1}$) and for MIL-68(In)—NHTr was 405 $m^2\ g^{-1}$. This curtail in surface area of MIL-68(In)—NHTr supports the successful attachment of the triazole moiety with the MIL-68(In)—$NH_2$ framework. The $CO_2$ adsorption isotherm for MIL-68(In)—NHTr was investigated at two different temperatures (273 K) and 298 K), with the maximum adsorption of 83.5 cubic centimeters per gram (cc $g^{-1}$) at 273 K (FIG. 13). $CO_2$ adsorption in the triazole appended MOF was more than MIL-68(In)—$NH_2$ (52.6 cc $g^{-1}$ at 273 K) due to the $CO_2$-phillic nature of the nitrogen-rich triazole moiety. Isosteric heat of adsorption ($Q_{st}$) was determined using the Clausius-Clapeyron equation and $CO_2$ adsorption isotherm at 273 K and 298 K (FIG. 14). The $Q_{st}$ value of $CO_2$ for MIL-68(In)—NHTr was determined to be 32.5 kilojoules per mol (kJ $mol^{-1}$), indicating a strong interaction between $CO_2$ and MIL-68(In)—NHTr. To interpret the structural features of MIL-68(In)—NHTr and its basic characteristics compared to MIL-68(In)—$NH_2$, $CO_2$-temperature-programmed desorption ($CO_2$-TPD) was carried out (FIG. 15). Basicity in these kinds of MOFs are weak (323-450 K) and medium to strong (450-773 K). $CO_2$-TPD of the MIL-68 (In)—NHTr showed a TPD peak around 554 K which corresponds to the medium Lewis basic sites due to the presence of triazole. In contrast, MIL-68(In)—$NH_2$ showed meager weak and medium basicity around 400 K to 550 K.

Catalysis

Catalysis for Synthesis of Oxazolidinones from Aromatic Amines, Epoxides, and $CO_2$.

Three-component reaction of 1,2-epoxyhexane with aniline and $CO_2$ was chosen as the model reaction to optimize the maximum conversion to oxazolidinone. The maximum conversion of 87% was obtained with MIL-68(In)—NHTr. MIL-68(In)—NHTr was screened for further catalysis experiments under an overall optimal reaction condition of 1 bar of $CO_2$ at 85° C. for 12 hours. To investigate the versatility of this catalyst, reactions with various amines were conducted and the results are compiled in Table 1.

TABLE 1

Cycloaddition reaction of $CO_2$ with different aromatic amines and 1,2-epoxyhexane in presence of MIL-68(In)-NHTr as catalysts.[a]

| Entry | Aromatic Amine | Product | Yield (%)[b] |
|---|---|---|---|
| 1 | 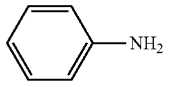 A1 | 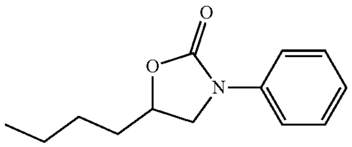 C1 | 87 |
| 2 | 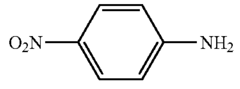 A2 | 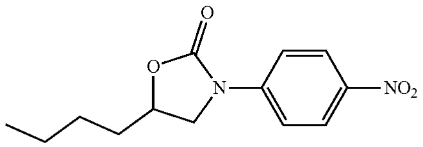 C2 | 94 |
| 3 | 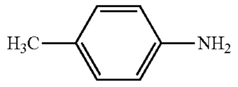 A3 | 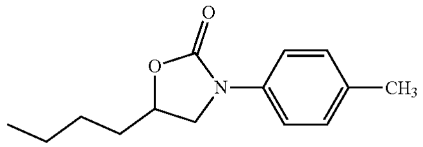 C3 | 83 |
| 4 | 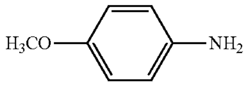 A4 | 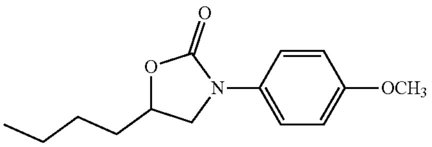 C4 | 80 |

TABLE 1-continued

Cycloaddition reaction of $CO_2$ with different aromatic amines and 1,2-epoxyhexane in presence of MIL-68(In)-NHTr as catalysts.[a]

| Entry | Aromatic Amine | Product | Yield (%)[b] |
|---|---|---|---|
| 5 | 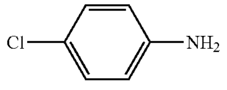 A5 | 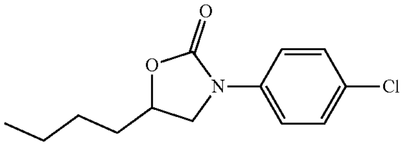 C5 | 91 |
| 6 | 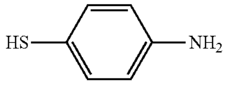 A6 | 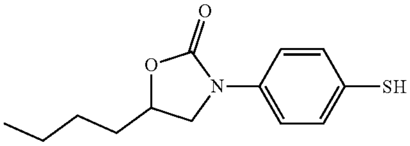 C6 | 81 |
| 7 | 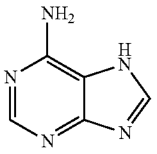 A7 | 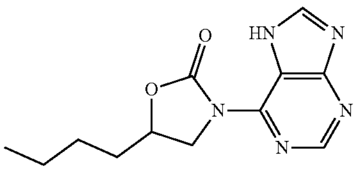 C7 | 70 |
| 8 | 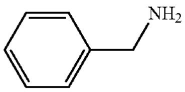 A8 | No reaction C8 | |

[a]Reaction conditions: 1,2-epoxyhexane (6.0 mmol), aromatic amine (2.0 mmol), solvent-free, catalyst (70 mg), $CO_2$ (1 bar), 12 h, 85° C.
[b]Isolated yield calculated with respect to A. Determined by $^1H$ NMR spectroscopy.

It was observed that anilines with electron-withdrawing group such as ($-NO_2$) gave a higher yield of 94% as compared to the anilines with electrondonating group ($-CH_3$, yield 83% and $-OCH_3$, yield 80%). The activity of MIL-68(In)—NHTr with the amine group of nitrogen rich heteroaromatic adenine ring was checked. This produced an adenine based oxazolidinone in 70% yield. The comparative low yield is due to the bulkiness of the aromatic amine and the overall the electron donating nature of the adenine ring. This catalyst failed to give any product with benzylamine. Different epoxides were also reacted with aniline in the presence of MIL-68(In)—NHTr and the outcome is summarized in Table 2.

TABLE 2

Cycloaddition reaction of $CO_2$ with different epoxides and aniline in presence of MIL-68(In)-NHTr as catalyst.[a]

| Entry | Epoxides | Product | Yield (%)[b] |
|---|---|---|---|
| 1 | 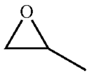 B2 | 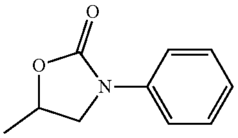 C9 | 90 |
| 2 | 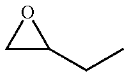 B3 | 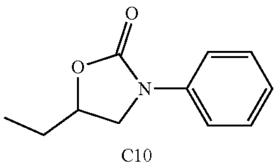 C10 | 89 |

TABLE 2-continued

Cycloaddition reaction of $CO_2$ with different epoxides and aniline in presence of MIL-68(In)-NHTr as catalyst.[a]

| Entry | Epoxides | Product | Yield (%)[b] |
|---|---|---|---|
| 3 | 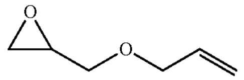 B4 | 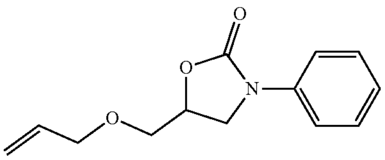 C11 | 87 |
| 4 | 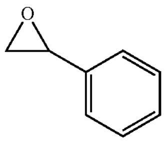 B5 | 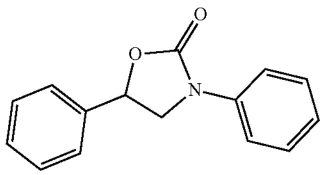 C12 | 78 |
| 5 | 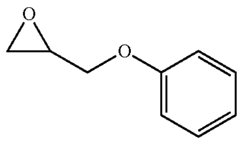 B6 | 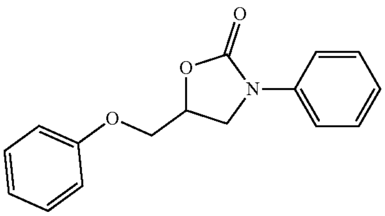 C13 | 85 |
| 6 | 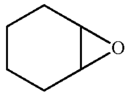 B7 | 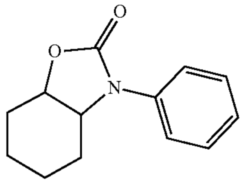 C14 | 73 |

[a]Reaction conditions: Epoxides (6.0 mmol), aniline (2.0 mmol), solvent-free, catalyst (70 mg), $CO_2$ (1 bar), 12 h, 85° C.
[b]Isolated yield calculated with respect to A. Determined by $^1H$ NMR spectroscopy.

Figure 16:
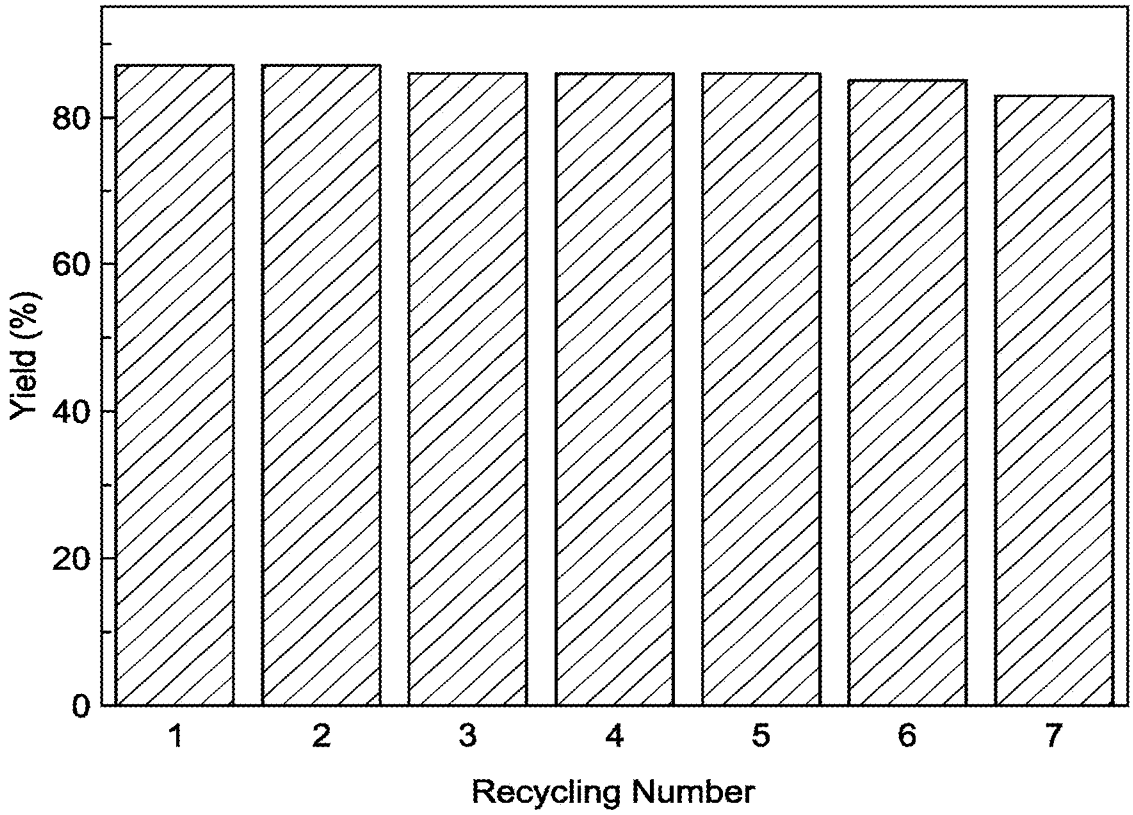
FIG. 16 depicts recycle tests with the MIL-68(In)—NHTr for a reaction of $CO_2$ with aniline and 1,2-epoxyhexane to form oxazolidinone, according to embodiments of the present disclosure.

It was observed that the monosubstituted aliphatic and aromatic epoxides gave a good yield of oxazolidinone with aniline (90-78%). The reaction also proceeded smoothly with bulky disubstituted epoxides such as cyclohexane oxide in the presence of this catalyst giving the corresponding oxazolidinone in 73% yield. In each reaction, only the 5-substituted oxazolidinones were obtained and not 4-substituted oxazolidinones or a mixture of two, probably due to steric hindrance between the aromatic amines, the epoxide side chain, and the structural framework of the MIL-68 (In)—NHTr. Recyclability is an important parameter for a heterogeneous catalyst. MIL-68(In)—NHTr can be easily separated from the reaction mixture by centrifugation and then wash with methanol three times and activated by drying at 100° C. The recycle performance of MIL-68(In)—NHTr was studied and is shown in FIG. 16. This catalyst can be reused for seven consecutive cycles without any obvious loss in catalytic activity. The PXRD pattern shows that the crystallinity of MIL-68(In)—NHTr remain intact for seven cycles.

In the present disclosure, the indium-based bifunctional MOF catalyst, MIL-68(In)—NHTr was prepared by coupling the triazole to the main framework of the MIL-68 (In)—$NH_2$. It acts as a single-site acid-base catalyst for $CO_2$ fixation through cycloaddition reaction of $CO_2$ with epoxides and aromatic amines in the synthesis of oxazolidinone. The catalyst was used under ambient pressure, in the absence of cocatalysts, is recyclable for seven cycles and does not produced any extra byproducts. The catalyst was successfully applicable for a variety of epoxides and aromatic amines with good yield.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of fixating carbon dioxide ($CO_2$) to form a substituted oxazolidinone, comprising:

mixing a metal-organic framework (MOF), at least one epoxide, and at least one aromatic amine to form a mixture; and contacting the mixture with a gas stream containing $CO_2$ to react the $CO_2$ in the gas stream with the epoxide and the aromatic amine to form a substituted oxazolidinone;

wherein the MOF is a MIL-68(In)—X MOF;

wherein X is of formula (I):

(I)

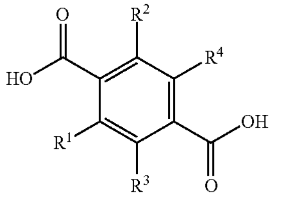

wherein:

at least one of $R^1$ to $R^4$ is an amine-containing group; and $R^1$ to $R^4$ are independently an amine-containing group or a hydrogen.

2. The method of claim 1, wherein X is:

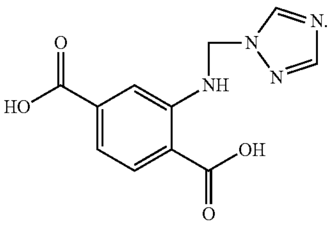 [SMILES: O=C(O)c1ccc(C(=O)O)c(NCn2cncn2)c1]

3. The method of claim 1, wherein the MIL-68(In)—X MOF comprises a terephthalate linker with a triazole-based moiety.

4. The method of claim 3, further comprising:

forming the MIL-68(In)—X MOF by functionalizing the terephthalate linker with the triazole-based moiety;

wherein the functionalizing includes reacting a terephthalic acid, a 1,2,4-triazole moiety, and formaldehyde to form a first compound; and hydrolyzing the first compound under alkaline conditions to form the terephthalate linker with the triazole-based moiety.

5. The method of claim 1, comprising:

repeating the contacting in the presence of the MIL-68 (In)—X MOF at least 5 times and up to 7 times wherein the yield of a final contacting is at least 95 percent of the yield of a first contacting based on an oxazolidinone product yield based on a mol percent.

6. The method of claim 1, wherein the MIL-68(In)—X MOF is in the form of particles having a surface area of 350-450 square meter per gram ($m^2$ $g^{-1}$).

7. The method of claim 1, wherein the MIL-68(In)—X MOF has an average carbon dioxide uptake of 40 to 90 gram per cubic centimeter (cc $g^{-1}$) at 1 bar at 273 kelvin (K).

8. The method of claim 1, wherein the MIL-68(In)—X MOF has an average isosteric heat of adsorption of 20 to 40 kilojoules per mole (kJ $mol^{-1}$).

9. The method of claim 1, wherein the epoxide is at least one selected from a group consisting of 1,2-epoxyhexane, 1,2-epoxypropane, 1,2-epoxybutane, allyl glycidyl ether, styrene oxide, phenyl glycidyl ether, and epoxycyclohexane.

10. The method of claim 1, wherein the aromatic amine is at least one selected from a group consisting of aniline, 4-nitroaniline, toluidine, para-anisidine, 4-chloroaniline, 4-aminothiophenol, adenine, and benzylamine.

11. The method of claim 1, wherein the mixture has a 1:1 to 1:5 molar ratio of the MIL-68(In)—X MOF to the aromatic amine.

12. The method of claim 1, wherein the mixture has a 1:1 to 1:10 molar ratio of the aromatic amine to the epoxide.

13. The method of claim 1, wherein the contacting occurs at a temperature of 40 to 150° C.

14. The method of claim 1, wherein the contacting occurs at a pressure of 0.5 to 10 bar of carbon dioxide.

15. The method of claim 1, wherein the contacting occurs for 8 to 20 hours.

16. The method of claim 1, wherein 65 to 95 percent of the aromatic amine is converted into the substituted oxazolidinone based on a mol percent.

17. The method of claim 1, wherein the MIL-68(In)—X MOF is microporous.

18. The method of claim 1, wherein the percent yield is calculated by proton nuclear magnetic resonance spectroscopy.

19. The method of claim 1, wherein:

the substituted oxazolidinone is of formula (II);

(II)

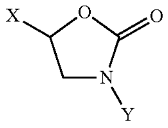

wherein

X is selected from a group consisting of an alkyl chain, an alkoxy group, an aromatic group, a methoxybenzene, and a cyclohexane; and Y is selected from a group consisting of a benzene, a para-substituted benzene, and an adenine.

20. The method of claim 1, wherein a cocatalyst is not present.

* * * * *